(12) United States Patent
Imwinkelried et al.

(10) Patent No.: US 9,066,999 B2
(45) Date of Patent: Jun. 30, 2015

(54) LEAN ELECTROLYTE FOR BIOCOMPATIBLE PLASMAELECTROLYTIC COATINGS ON MAGNESIUM IMPLANT MATERIAL

(71) Applicant: DePuy Synthes Products, Inc., Raynham, MA (US)

(72) Inventors: Thomas Imwinkelried, Seltisberg (CH); Peter Kurze, Nideggen (DE); Stefan Beck, Niederdorf (CH); Dora Banerjee, Kerpen (DE); Tamara Schwarz, Bergheim (DE)

(73) Assignee: DePuy Synthes Products, Inc., Raynham, MA (US)

( * ) Notice: Subject to any disclaimer, the term of this patent is extended or adjusted under 35 U.S.C. 154(b) by 282 days.

(21) Appl. No.: 13/670,803

(22) Filed: Nov. 7, 2012

(65) Prior Publication Data

US 2013/0116696 A1    May 9, 2013

Related U.S. Application Data

(60) Provisional application No. 61/556,563, filed on Nov. 7, 2011.

(51) Int. Cl.
| | |
|---|---|
| *C25D 11/30* | (2006.01) |
| *C25D 11/02* | (2006.01) |
| *A61L 31/02* | (2006.01) |
| *A61L 31/08* | (2006.01) |
| *A61L 31/14* | (2006.01) |

(52) U.S. Cl.
CPC ............. *A61L 31/022* (2013.01); *A61L 31/088* (2013.01); *A61L 31/148* (2013.01); *A61L 2400/18* (2013.01); *C25D 11/026* (2013.01); *C25D 11/30* (2013.01); *C25D 11/022* (2013.01)

(58) Field of Classification Search
CPC .............................. C25D 11/026; C25D 11/30
USPC ......................................................... 205/321
See application file for complete search history.

(56) References Cited

U.S. PATENT DOCUMENTS

| | | | | |
|---|---|---|---|---|
| 5,385,662 | A * | 1/1995 | Kurze et al. ................... | 205/316 |
| 6,280,598 | B1 * | 8/2001 | Barton et al. ................. | 205/210 |
| 2006/0016690 | A1 | 1/2006 | Ostrovsky | |

FOREIGN PATENT DOCUMENTS

| | | |
|---|---|---|
| EP | 0333048 A1 | 9/1989 |
| EP | 2189170 A1 | 5/2010 |

OTHER PUBLICATIONS

Search Report and Written Opinion that was issued on Feb. 22, 2013 in PCT Application No. PCT/US2012/63815 (10 sheets).

*Primary Examiner* — Bryan D. Ripa
(74) *Attorney, Agent, or Firm* — Baker & Hostetler LLP

(57) ABSTRACT

The present disclosure is directed, at least in part, to a method of producing ceramic layers on magnesium and its alloys, a magnesium implant with a ceramic layer made by the method, and a magnesium implant having a biocompatible ceramic layer substantially free of material which impairs the biocompatibility of said biocompatible ceramic layer. In an exemplary embodiment, the method of producing ceramic layers on magnesium and its alloys, includes (a) immersing an implant and a metal sheet into the aqueous electrolyte bath, said aqueous electrolyte bath including: ammoniac, diammonium hydrogen phosphate and urea, and wherein the implant is made of magnesium or its alloy; (b) performing a anodic oxidation by passing a current between the implant, the metal sheet and through the aqueous electrolyte bath, wherein the implant is connected to a positive pole of a current source and the metal sheet is connected to a negative pole of the current source; (c) applying a current density selected to form sparks on said implant, to thereby form a ceramic layer on said implant.

7 Claims, 12 Drawing Sheets

LEAN ELECTROLYTE FOR BIOCOMPATIBLE PLASMAELECTROLYTIC COATINGS ON MAGNESIUM IMPLANT MATERIAL

CROSS-REFERENCE TO RELATED APPLICATIONS

This application claims the benefit of U.S. Provisional Patent Application No. 61/556,563, filed Nov. 7, 2011, which is incorporated herein by reference in its entirety.

FIELD OF THE INVENTION

The present disclosure is directed, at least in part, to a method of producing ceramic layers on magnesium and its alloys, a magnesium implant with a ceramic layer made by the method, and a magnesium implant having a biocompatible ceramic layer substantially free of material which impairs the biocompatibility of said biocompatible ceramic layer.

BACKGROUND OF THE INVENTION

Traditional methods of osteosynthesis and osteotomy used permanent metal implants made of steel or titanium. However, since these durable metal implants represent a foreign body, patients receiving them are potentially at a greater risk of a local inflammation. Moreover, while these implants tend to permanently protect healing bones against mechanical exposure, this stress shielding-effect actually forestalls the stabilization of the bone tissue that needs mechanical loads to obtain and maintain its rigidity. One solution to this problem requires a follow up surgery to remove the permanent metal implants. But such follow up surgeries increase the risk of re-fracture of the healing bones, and/or cause the patients to suffer unnecessary inconveniences, including delayed recovery and incurrence of additional expenses.

Alternative implants using metallic magnesium and certain magnesium alloys have been shown to be biodegradable and potentially suitable for medical applications. However, because of the electrochemical activity of magnesium, the corrosion rates of such implants are highly dependent on factors such as implant composition, type of environment or site of implantation, and the surface condition of the implant (treated or untreated). When exposed to air the surface of untreated magnesium implants reacts with oxygen, building up a layer of magnesium hydroxide on the surface, thereby slowing down further chemical reactions. In saline media, such as in the environment of the human organism, untreated magnesium implants initially corrode very rapidly, producing high amounts of hydrogen gas and magnesium hydroxide. Uncontrolled corrosion of magnesium implants can cause premature failure of loaded implants due to stress corrosion cracking and/or due to corrosion fatigue. Moreover, because of the initial high gas release subcutaneous gas cavities might form. Thus, a need exists for magnesium based implants with improved corrosion performance.

The initial high gas release and the formation of gas bubbles in vivo can potentially be avoided by application of a coating to the surface of the magnesium implants prior to implantation. The coating would retard the rate of corrosion of the metal implants, thereby stabilizing the rate of gas release due to corrosion of the implants. Several attempts to improve corrosion performance of magnesium have been reported, including coating by anodization in solutions of concentrated alkaline hydroxides, or in solutions of hydrofluoric acid or acid fluoride salts.

Anodization of magnesium using base solutions of concentrated alkaline hydroxides is generally provided through the supply of a DC current at a range of 50 volts to 150 volts. A coating is formed on the magnesium through the formation of sparks within the bath. The tracking of the sparks across the surface of the magnesium element slowly places the coating onto the magnesium. The use of sparks throughout the process leads to a relatively high current usage and to significant heat absorption by the bath itself. Therefore, cooling may be necessary to reduce the temperature of the bath during the anodization process.

Use of hydrofluoric acid or acid fluoride salts in anodization of magnesium results in the formation of a protective layer of magnesium fluoride on the magnesium surface. This protective layer is not soluble in water and thus prevents further reaction of the magnesium metal.

Other methods for anodization of magnesium or alloys of magnesium incorporate other species into the film as it is formed on the surface of the magnesium. Some anodization processes use silicates and others use various ceramic materials.

However, many of the reported magnesium coatings might be toxic. Therefore, a need exists for biocompatible coating compositions and coating processes will produce resorbable biomaterial onto the surface of magnesium implants that cannot completely prevent the degradation process, so the performance of the implants can be modulated by how the implant is coated and/or the corrosion characteristic of the base material used to coat the implants.

BRIEF SUMMARY OF THE INVENTION

An aspect of the present disclosure provides for a method of producing ceramic layers on magnesium and its alloys. An exemplary method in accordance with the present invention comprises the steps of: (a) immersing an implant and a metal sheet into the aqueous electrolyte bath, said aqueous electrolyte bath consisting essentially of: ammoniac ($NH_3$), diammonium hydrogen phosphate (($NH_4$)$_2$$HPO_4$) and urea ($CH_4N_2O$), and wherein the implant is made of magnesium or its alloy; (b) performing a anodic oxidation by passing a current between the implant, the metal sheet and through the aqueous electrolyte bath, wherein the implant is connected to a positive pole of a current source and the metal sheet is connected to a negative pole of the current source; (c) applying a current density selected to form sparks on said implant, to thereby form a ceramic layer on said implant. In an embodiment, the ammoniac concentration at 25 vol. % ranges from 1.0 mol/L to 6.0 mol/L, the diammonium hydrogen phosphate concentration ranges from 0.05 mol/L to 0.2 mol/L; and the urea concentration ranges from 0.01 mol/L to 1.0 mol/L.

Another exemplary method in accordance with the present invention comprises the steps of: (a) immersing an implant and a metal sheet into the aqueous electrolyte bath, said aqueous electrolyte bath consisting of: ammoniac, diammonium hydrogen phosphate and urea, and wherein the implant is made of magnesium or its alloy; (b) performing a anodic oxidation by passing a current between the implant, the metal sheet and through the aqueous electrolyte bath, wherein the implant is connected to a positive pole of a current source and the metal sheet is connected to a negative pole of the current source; (c) applying a current density selected to form sparks on said implant, to thereby form a ceramic layer on said implant. In an embodiment, the ammoniac concentration at 25 vol. % ranges from 1.0 mol/L to 6.0 mol/L, the diammonium hydrogen phosphate concentration ranges from 0.05 mol/L to 0.2 mol/L; and the urea concentration ranges from 0.01 mol/L to 1.0 mol/L.

In an embodiment, the aqueous electrolyte bath has a pH value ranging from 10.3 to 11.6 and a temperature ranging from 18° C. to 22° C. In another embodiment, the current density is at least 1 A/dm². In another embodiment, the current density ranges from 1 A/dm² to 3 A/dm². In yet another embodiment, the coating is selectively applied to the implant by electrically insulating areas of the surface which are not to be coated. In another embodiment, electric insulation of the areas which are not to be coated is achieved by applying a lacquer, film or foil or the like which can be removed after the coating process (e.g. by manual delamination).

Another aspect of the present disclosure provides for a magnesium implant with a ceramic layer made by exemplary methods according to the present invention. In an exemplary embodiment of said magnesium implant with a ceramic layer, said layer is an oxide, hydroxide or phosphate ceramic layer or a combination thereof and has a thickness of up to 50 µm. In another embodiment of the magnesium implant with a ceramic layer, said ceramic layer has a thickness ranging from 2 µm to 20 µm. In another embodiment of the magnesium implant with a ceramic layer, said ceramic layer selected from the group consisting of: MgO, Mg(OH)$_2$, Mg$_3$(PO$_4$)$_2$ and oxides of alloying elements of magnesium. In yet another embodiment of the magnesium implant with a ceramic layer, said ceramic layer improves bone tissue adhesion compared to non-coated magnesium implant and is substantially free of substances which impair biocompatibility. In an embodiment of the magnesium implant with a ceramic layer, said magnesium implant is substantially free of substances which impair biocompatibility. In one such embodiment, said substances comprise an amine decomposition product.

According to another exemplary embodiment of the magnesium implant of the present invention, said magnesium implant has a biocompatible ceramic layer substantially free of material which impairs the biocompatibility of said biocompatible ceramic layer, said biocompatible ceramic layer having a thickness of up to 50 µm. In one embodiment, said biocompatible ceramic layer includes a component selected from the group consisting of MgO, Mg(OH)$_2$, Mg$_3$(PO$_4$)$_2$, oxides of alloying elements of magnesium and combinations thereof. In one such embodiment, said material which impairs the biocompatibility of said biocompatible ceramic layer comprises an amine decomposition product.

In an embodiment of the magnesium implant with a ceramic layer, said implant delays and reduces hydrogen release, compared to a magnesium implant without said biocompatible oxide ceramic layer, when immersed in a simulated body fluid. In yet another embodiment of the magnesium implant with a ceramic layer, said hydrogen release is reduced with respect to the corroded mass of magnesium compared to a magnesium implant without said ceramic layer by 10% to 50% over an immersion period of up to 40 days.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention can be embodied in different forms and thus should not be construed as being limited to the embodiments set forth herein.

DETAILED DESCRIPTION OF THE INVENTION

Figure 1:
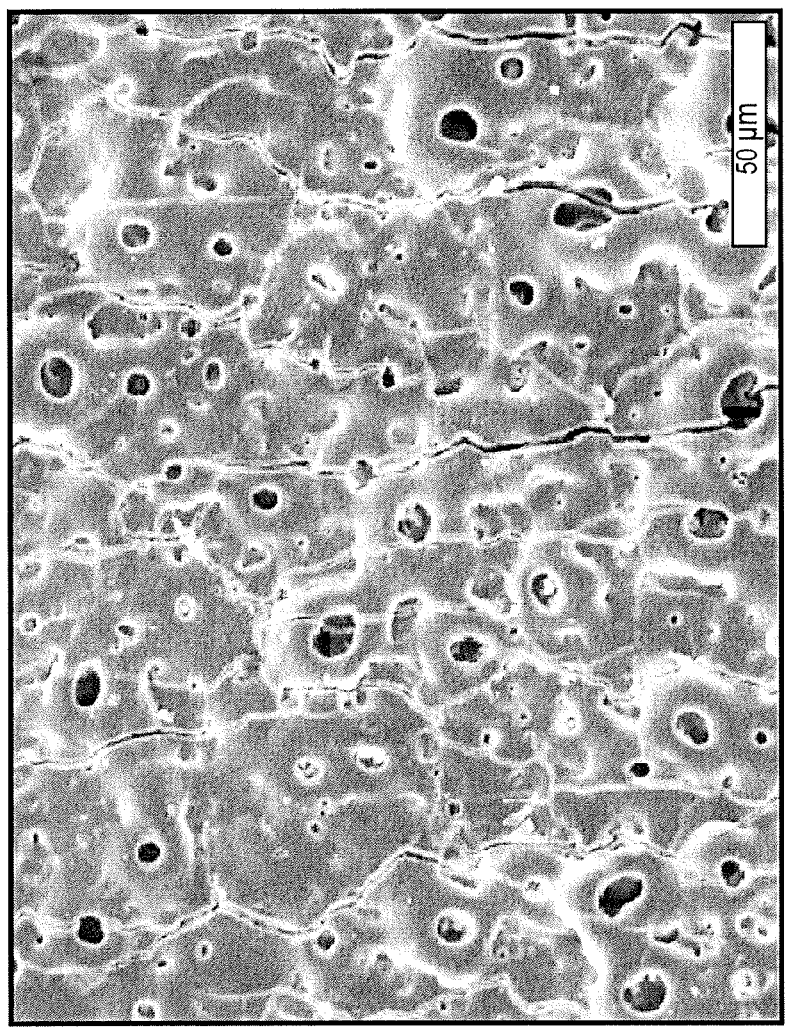
FIG. 1 is an SEM image of a coating according to an embodiment of the invention with coarse pores.

The present subject matter will now be described more fully hereinafter with reference to the accompanying Figures and Examples, in which representative embodiments are shown. The present subject matter can, however, be embodied in different forms and should not be construed as limited to the embodiments set forth herein. Rather, these embodiments are provided to describe and enable one of skill in the art. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entirety.

During the degradation of metallic magnesium implant, hydrogen gas and magnesium hydroxide are formed by the corrosion reaction. If the amount of released gas surpasses the absorption and diffusion capacity of the surrounding tissue, gas bubbles might form and are often visible on X-rays. The bare metal surface causes an initial increased release of gas right after implantation, but soon after the metal surface is covered with degradation products, the gas release rate stabilizes and might be low enough to allow sufficient gas transport. The application of a coating could avoid the initial high gas release and the formation of gas bubbles. Also, an adequate coating should effectively avoid premature failure of loaded implants due to stress corrosion cracking and/or corrosion fatigue. Moreover, a coating should be biocompatible and be obtainable without the use of toxic or potentially harmful substances.

Accordingly, an aspect of the present invention provides a method of producing ceramic layers on magnesium and its alloys. In some embodiments of the invention, the method includes exposing a magnesium or magnesium alloy implant to an aqueous electrolyte comprising, consisting of, or consisting essentially of: ammoniac, diammonium hydrogen phosphate and urea. In an embodiment, said method comprises (a) immersing an implant and a metal sheet into an aqueous electrolyte bath, said aqueous electrolyte bath consisting essentially of: ammoniac, diammonium hydrogen phosphate and urea, said implant being made of magnesium or its alloy; (b) performing an anodic oxidation by passing a current between said implant, said metal sheet and through said aqueous electrolyte bath, wherein said implant is connected to a positive pole of a current source and said metal sheet is connected to a negative pole of said current source; (c) applying a current density selected to form sparks on said implant, to thereby form a ceramic layer on said implant. For the purpose of this application, consisting essentially of shall mean that in addition to the recited components, the aqueous electrolyte bath may include other components that do not materially affect the characteristics of the ceramic layer of the magnesium implant. In some embodiments, such characteristics may include one or more of bone tissue adhesion of the implant, biocompatibility, absence of amine decomposition products, and reduced hydrogen gas evolution each compared to an uncoated magnesium implant.

In an embodiment, the ammoniac concentration at 25 vol. % ranges from 1.0 mol/L to 6.0 mol/L. In another embodiment, the diammonium hydrogen phosphate concentration ranges from 0.05 mol/L to 0.2 mol/L. In another embodiment the urea concentration ranges from 0.01 mol/L to 1.0 mol/L. In an embodiment, the ammoniac concentration at 25 vol. % ranges from 1.0 mol/L to 6.0 of and the diammonium hydrogen phosphate concentration ranges from 0.05 mol/L to 0.2 mol/L. In an embodiment, the ammoniac concentration at 25 vol. % ranges from 1.0 mol/L to 6.0 of and the urea concentration ranges from 0.01 mol/L to 1.0 mol/L. In an embodiment, the diammonium hydrogen phosphate concentration ranges from 0.05 mol/L to 0.2 mol/L and the urea concentration ranges from 0.01 mol/L to 1.0 mol/L.

In another exemplary embodiment, the present invention provides a method of producing ceramic layers on magnesium and its alloys, said method comprises (a) immersing an implant and a metal sheet into an aqueous electrolyte bath, said aqueous electrolyte bath consisting of: ammoniac, diammonium hydrogen phosphate and urea, said implant being made of magnesium or its alloy; (b) performing an anodic oxidation by passing a current between said implant, said metal sheet and through said aqueous electrolyte bath, wherein said implant is connected to a positive pole of a current source and said metal sheet is connected to a negative pole of said current source; (c) applying a current density selected to form sparks on said implant, to thereby form a ceramic layer on said implant.

In an embodiment, the ammoniac concentration at 25 vol. % ranges from 1.0 mol/L to 6.0 mol/L. In another embodiment, the diammonium hydrogen phosphate concentration ranges from 0.05 mol/L to 0.2 mol/L. In another embodiment the urea concentration ranges from 0.01 mol/L to 1.0 mol/L. In an embodiment, the ammoniac concentration at 25 vol. % ranges from 1.0 mol/L to 6.0 mol/L and the diammonium hydrogen phosphate concentration ranges from 0.05 mol/L to 0.2 mol/L. In an embodiment, the ammoniac concentration at 25 vol. % ranges from 1.0 mol/L to 6.0 mol/L and the urea concentration ranges from 0.01 mol/L to 1.0 mol/L. In an embodiment, the diammonium hydrogen phosphate concentration ranges from 0.05 mol/L to 0.2 mol/L and the urea concentration ranges from 0.01 mol/L to 1.0 mol/L.

In some embodiments of the methods, the ammoniac concentration at 25 vol. % is selected from the group consisting of 1.0 mol/L, 1.1 mol/L, 1.2 mol/L, 1.3 mol/L, 1.4 mol/L, 1.5 mol/L, 1.6 mol/L, 1.7 mol/L, 1.8 mol/L, 1.9 mol/L, 2 mol/L, 2.1 mol/L, 2.2 mol/L, 2.3 mol/L, 2.4 mol/L, 2.5 mol/L, 2.6 mol/L, 2.7 mol/L, 2.8 mol/L, 2.9 mol/L, 3 mol/L, 3.1 mol/L, 3.2 mol/L, 3.3 mol/L, 3.4 mol/L, 3.5 mol/L, 3.6 mol/L, 3.7 mol/L, 3.8 mol/L, 3.9 mol/L, 4 mol/L, 4.1 mol/L, 4.2 mol/L, 4.3 mol/L, 4.4 mol/L, 4.5 mol/L, 4.6 mol/L, 4.7 mol/L, 4.8 mol/L, 4.9 mol/L, 5 mol/L, 5.1 mol/L, 5.2 mol/L, 5.3 mol/L, 5.4 mol/L, 5.5 mol/L, 5.6 mol/L, 5.7 mol/L, 5.8 mol/L, 5.9 mol/L, 6 mol/L, and values in between. In some embodiments, the ammoniac concentration at 25 vol. % is at least 1.0 mol/L. In some embodiments, the ammoniac concentration at 25 vol. % is greater than 1.0 mol/L. In some embodiments, the ammoniac concentration at 25 vol. % is less than 6 mol/L. In some embodiments, the ammoniac concentration at 25 vol. % is no more than 6 mol/L.

In some embodiments of the methods, the diammonium hydrogen phosphate concentration is selected from the group consisting 0.05 mol/L, 0.06 mol/L, 0.07 mol/L, 0.08 mol/L, 0.09 mol/L, 0.1 mol/L, 0.11 mol/L, 0.12 mol/L, 0.13 mol/L, 0.14 mol/L, 0.15 mol/L, 0.16 mol/L, 0.17 mol/L, 0.18 mol/L, 0.19 mol/L, 0.2 mol/L, and values in between. In some embodiments, the diammonium hydrogen phosphate concentration is at least 0.05 mol/L. In some embodiments, the diammonium hydrogen phosphate concentration is greater than 0.05 mol/L. In some embodiments, the diammonium hydrogen phosphate concentration is less than 0.2 mol/L. In some embodiments, the diammonium hydrogen phosphate concentration is no more than 0.2 mol/L.

In some embodiments of the methods, the urea concentration is selected from the group consisting of 0.01 mol/L, 0.02 mol/L, 0.03 mol/L, 0.04 mol/L, 0.05 mol/L, 0.06 mol/L, 0.07 mol/L, 0.08 mol/L, 0.09 mol/L, 0.1 mol/L, 0.11 mol/L, 0.12 mol/L, 0.13 mol/L, 0.14 mol/L, 0.15 mol/L, 0.16 mol/L, 0.17 mol/L, 0.18 mol/L, 0.19 mol/L, 0.2 mol/L, 0.21 mol/L, 0.22 mol/L, 0.23 mol/L, 0.24 mol/L, 0.25 mol/L, 0.26 mol/L, 0.27 mol/L, 0.28 mol/L, 0.29 mol/L, 0.3 mol/L, 0.31 mol/L, 0.32 mol/L, 0.33 mol/L, 0.34 mol/L, 0.35 mol/L, 0.36 mol/L, 0.37 mol/L, 0.38 mol/L, 0.39 mol/L, 0.4 mol/L, 0.41 mol/L, 0.42 mol/L, 0.43 mol/L, 0.44 mol/L, 0.45 mol/L, 0.46 mol/L, 0.47 mol/L, 0.48 mol/L, 0.49 mol/L, 0.5 mol/L, 0.51 mol/L, 0.52 mol/L, 0.53 mol/L, 0.54 mol/L, 0.55 mol/L, 0.56 mol/L, 0.57 mol/L, 0.58 mol/L, 0.59 mol/L, 0.6 mol/L, 0.61 mol/L, 0.62 mol/L, 0.63 mol/L, 0.64 mol/L, 0.65 mol/L, 0.66 mol/L, 0.67 mol/L, 0.68 mol/L, 0.69 mol/L, 0.7 mol/L, 0.71 mol/L, 0.72 mol/L, 0.73 mol/L, 0.74 mol/L, 0.75 mol/L, 0.76 mol/L, 0.77 mol/L, 0.78 mol/L, 0.79 mol/L, 0.8 mol/L, 0.81 mol/L, 0.82 mol/L, 0.83 mol/L, 0.84 mol/L, 0.85 mol/L, 0.86 mol/L, 0.87 mol/L, 0.88 mol/L, 0.89 mol/L, 0.9 mol/L, 0.91 mol/L, 0.92 mol/L, 0.93 mol/L, 0.94 mol/L, 0.95 mol/L, 0.96 mol/L, 0.97 mol/L, 0.98 mol/L, 0.99 mol/L, 1 mol/L, and values in between. In some embodiments, the urea concentration is at least 0.01 mol/L. In some embodiments, the urea concentration is greater than 0.01 mol/L. In some embodiments, the urea concentration is less than 1 mol/L. In some embodiments, the urea concentration is no more than 1 mol/L.

In an embodiment, the aqueous electrolyte bath has a pH value ranging from about 6 to about 14, from about 6 about 13, from about 6 to about 12, from about 6 to about 11, from about 6 to about 10, from about 6 to about 9, from about 6 to about 8, or from about 6 to about 7. In another embodiment, the aqueous electrolyte bath has a pH value ranging from about 7 to about 14, from about 7 about 13, from about 7 to about 12, from about 7 to about 11, from about 7 to about 10, from about 7 to about 9, or from about 7 to about 8. In another embodiment, the aqueous electrolyte bath has a pH value ranging from about 8 to about 14, from about 8 about 13, from about 8 to about 12, from about 8 to about 11, from about 8 to about 10, or from about 8 to about 9. In another embodiment, the aqueous electrolyte bath has a pH value ranging 9 to about 14, from about 9 about 13, from about 9 to about 12, from about 9 to about 11, or from about 9 to about 10. In another embodiment, the aqueous electrolyte bath has a pH value ranging 10 to about 14, from about 10 about 13, from about 10 to about 12, or from about 10 to about 11. In another embodiment, the aqueous electrolyte bath has a pH value ranging 11 to about 14, from about 11 about 13, or from about 11 to about 12. In some embodiments, the aqueous electrolyte bath has a pH value of greater than 6. In some embodiments, the aqueous electrolyte bath has a pH value of at least 6, at least 7, at least 8, at least 9, at least 10, or at least 11. In some embodiments, the aqueous electrolyte bath has a pH value of less than 14, less than 13, or less than 12. In some embodiments, the aqueous electrolyte bath has a pH value of no more than 14. In yet another embodiment, the aqueous electrolyte bath has a pH value ranging from 10.3 to 11.6.

In an embodiment, the aqueous electrolyte bath has a temperature ranging from about 0° C. to about 5° C., from about 10° C. to about 15° C., from about 20° C. to about 25° C., from about 30° C. to about 35° C., from about 40° C. to about 45° C., from about 45° C. to about 50° C., from about 0° C. to about 5° C., from about 0° C. to about 10° C., from about 0° C. to about 15° C., from about 0° C. to about 20° C., from about 0° C. to about 25° C., from about 0° C. to about 30° C. to about 35° C., from about 0° C. to about 40° C., from about 0° C. to about 45° C., from about 0° C. to about 45° C., from about 0° C. to about 50° C., from about 5° C. to about 10° C., from about 5° C. to about 15° C., from about 5° C. to about 20° C., from about 5° C. to about 25° C., from about 5° C. to about 30° C., from about 5° C. to about 35° C., from about 5° C. to about 40° C., from about 5° C. to about 45° C., from 5° C. to about 50° C., from about 10° C. to about 15° C., from about 10° C. to about 20° C., from about 10° C. to about 25° C., from about 10° C. to about 30° C., from about 10° C. to about 35° C., from about 10° C. to about 40° C., from about 10° C. to about 45° C., from 10° C. to about 50° C., from about 15° C. to about 20° C., from about 15° C. to about 25° C., from about 15° C. to about 30° C., from about 15° C. to about 35° C., from about 15° C. to about 40° C., from about 15° C. to about 45° C., from 15° C. to about 50° C., from about 20° C. to about 25° C., from about 20° C. to about 30° C., from about 20° C. to about 35° C., from about 20° C. to about 40° C., from about 20° C. to about 45° C., from 20° C. to about 50° C., from about 25° C. to about 30° C., from about 25° C. to about 35° C., from about 25° C. to about 40° C., from about 25° C. to about 45° C., from 25° C. to about 50° C., from about 30° C. to about 35° C., from about 30° C. to about 40° C., from about 30° C. to about 45° C., from 30° C. to about 50° C., from about 35° C. to about 40° C., from about 35° C. to about 45° C., from about 35° C. to about 45° C., from 35° C. to about 50° C., from about 40° C. to about 45° C., from 40° C. to about 50° C., or from 45° C. to about 50° C. In another embodiment, the aqueous electrolyte bath has a temperature ranging from 18° C. to 22° C.

In an embodiment, the current density ranges from 1 $A/dm^2$ to 1.2 $A/dm^2$, from 1 $A/dm^2$ to 1.3 $A/dm^2$, from 1 $A/dm^2$ to 1.4 $A/dm^2$, from 1 $A/dm^2$ to 1.5 $A/dm^2$, from 1 $A/dm^2$ to 1.6 $A/dm^2$, from 1 $A/dm^2$ to 1.7 $A/dm^2$, from 1 $A/dm^2$ to 1.8 $A/dm^2$, from 1 $A/dm^2$ to 1.9 $A/dm^2$, from 1 $A/dm^2$ to 2 $A/dm^2$, from 1 $A/dm^2$ to 2.1 $A/dm^2$, from 1 $A/dm^2$ to 2.2 $A/dm^2$, from 1 $A/dm^2$ to 2.3 $A/dm^2$, from 1 $A/dm^2$ to 2.4 $A/dm^2$, from 1 $A/dm^2$ to 2.5 $A/dm^2$, from 1 $A/dm^2$ to 2.6 $A/dm^2$, from 1 $A/dm^2$ to 2.7 $A/dm^2$, from 1 $A/dm^2$ to 2.8 $A/dm^2$, from 1 $A/dm^2$ to 2.9 $A/dm^2$, or from 1 $A/dm^2$ to 3 $A/dm^2$. In another embodiment, the current density is at least 1 $A/dm^2$. In some embodiments, the current density is greater than 1 $A/dm^2$. In some embodiments, the current density is less than 3 $A/dm^2$. In some embodiments, the current density is no more than 3 $A/dm^2$.

In an embodiment, a method of the present invention provides for forming a ceramic coating on selected portions of the surface area of the implant. In an embodiment, selected portions of the surface area of the implant are electrically insulated to allow selective anodization of the regions of the surface of the implant that are not electrically insulated. In an embodiment, the electric insulation of the areas which are not to be coated is achieved by applying a lacquer, film or foil or the like to the desired regions of the surface area of the implant, and subsequent to the coating process, the applied lacquer, film or foil is removed (by manual delamination, for example).

It will be understood by those of ordinary skill in the art that a wide variety of coating patterns may be designed and applied to implants. Those of ordinary skill in the art that would also know that the position and dimensions of the selectively coated regions of the surface area of the implant may be varied to modulate the corrosion performance the coated implant. For example, the selectively coated regions of the implant would be expected to degrade at a slower rate than the uncoated regions because the coat the reactants must first penetrate the coat or erode it before reaching the coated surface of the reactive surface of the implant.

In an embodiment of the magnesium implant with a ceramic layer, said ceramic layer comprises an oxide, hydroxide, phosphate or combinations thereof. In an embodiment of the magnesium implant with a ceramic layer, said ceramic layer comprises an oxide. In an embodiment of the magnesium implant with a ceramic layer, said ceramic layer comprises a hydroxide. In an embodiment of the magnesium implant with a ceramic layer, said ceramic layer comprises phosphate. In an embodiment of the magnesium implant with a ceramic layer, said ceramic layer comprises an oxide and a hydroxide. In an embodiment of the magnesium implant with a ceramic layer, said ceramic layer comprises an oxide and a phosphate. In an embodiment of the magnesium implant with a ceramic layer, said ceramic layer comprises a hydroxide and a phosphate. In another embodiment of the magnesium implant with a ceramic layer, said ceramic layer comprises an oxide, a hydroxide and a phosphate. In another embodiment of the magnesium implant with a ceramic layer, said ceramic layer is selected from the group consisting of: MgO, $Mg(OH)_2$, $Mg_3(PO_4)_2$ and oxides of alloying elements of magnesium.

In an embodiment of the magnesium implant with a ceramic layer, said ceramic layer has a thickness of up to 50 µm. In an embodiment of the magnesium implant with a ceramic layer, said ceramic layer has a thickness ranging from about 1 µm to about 5 µm, from about 10 µm to about 15 µm, from about 20 µm to about 25 µm, from about 30 µm to about 35 µm, from about 40 µm to about 45 µm, from about 45 µm to about 50 µm, from about 1 µm to about 5 µm, from about 1 µm to about 10 µm, from about 1 µm to about 15 µm, from about 1 µm to about 20 µm, from about 1 µm to about 25 µm, from about 1 µm to about 30 µm to about 35 µm, from about 1 µm to about 40 µm, from about 1 µm to about 45 µm, from about 1 µm to about 45 µm, from 1 µm to about 50 µm, from about 5 µm to about 10 µm, from about 5 µm to about 15 µm, from about 5 µm to about 20 µm, from about 5 µm to about 25 µm, from about 5 µm to about 30 µm, from about 5 µm to about 35 µm, from about 5 µm to about 40 µm, from about 5 µm to about 45 µm, from 5 µm to about 50 µm, from about 10 µm to about 15 µm, from about 10 µm to about 20 µm, from about 10 µm to about 25 µm, from about 10 µm to about 30 µm, from about 10 µm to about 35 µm, from about 10 µm to about 40 µm, from about 10 µm to about 45 µm, from 10 µm to about 50 µm, from about 15 µm to about 20 µm, from about 15 µm to about 25 µm, from about 15 µm to about 30 µm, from about 15 µm to about 35 µm, from about 15 µm to about 40 µm, from about 15 µm to about 45 µm, from 15 µm to about 50 µm, from about 20 µm to about 25 µm, from about 20 µm to about 30 µm, from about 20 µm to about 35 µm, from about 20 µm to about 40 µm, from about 20 µm to about 45 µm, from 20 µm to about 50 µm, from about 25 µm to about 30 µm, from about 25 µm to about 35 µm, from about 25 µm to about 40 µm, from about 25 µm to about 45 µm, from 25 µm to about 50 µm, from about 30 µm to about 35 µm, from about 30 µm to about 40 µm, from about 30 µm to about 45 µm, from 30 µm to about 50 µm, from about 35 µm to about 40 µm, from about 35 µm to about 45 µm, from about 35 µm to about 45 µm, from 35 µm to about 50 µm, from about 40 µm to about 45 µm, from 40 µm to about 50 µm, or from 45 µm to about 50 µm. In another embodiment, the magnesium implant with a ceramic layer, said ceramic layer has a thickness ranging from 2 µm to 20 µm. In some embodiments, the ceramic layer is at least or greater than 1 µm in thickness, at least or greater than 2 µm in thickness, at least or greater than 5 µm in thickness, at least or greater than 10 µm in thickness, at least or greater than 15 µm in thickness, at least or greater than 20 µm in thickness, at least or greater than 25 µm in thickness, at least or greater than 30 µm in thickness, at least or greater than 35 µm in thickness, at least or greater than 40 µm in thickness, at least or greater than 45 µm in thickness, or at least or greater than 50 µm in thickness. In some embodiments, the ceramic layer is no more than 50 µm in thickness.

The magnesium implant with a ceramic layer made by the methods of the present invention advantageously has a ceramic layer that not only improves bone tissue adhesion, but also is substantially free of substances which impair the biocompatibility. In an embodiment, the biocompatible ceramic layer is substantially free of material which impairs the biocompatibility of said biocompatible ceramic layer. In an embodiment, said biocompatible ceramic layer typically will have a thickness of up to 50 µm. In one such embodiment, said material which impairs the biocompatibility of said biocompatible ceramic layer comprises an amine decomposition product. In another embodiment, biocompatible ceramic layer includes a component selected from the group consisting of MgO, $Mg(OH)_2$, $Mg_3(PO_4)_2$, oxides of alloying elements of magnesium and combinations thereof. Another advantage of the magnesium implant with a ceramic layer made by the methods of the present invention is that said implant delays and/or reduces hydrogen release, compared to a magnesium implant without said biocompatible ceramic layer, when immersed in a simulated body fluid, for example.

Accordingly, in an embodiment of the magnesium implant with a ceramic layer according to the present invention, said ceramic layer reduces hydrogen release with respect to the corroded mass of magnesium compared to a magnesium implant without said ceramic layer by 10% to 50% over an immersion period of up to 40 days. In an embodiment, said ceramic coated magnesium implant reduces hydrogen release with respect to the corroded mass of magnesium compared to a magnesium implant without said ceramic layer by from about 10% to about 15%, from about 10% to about 20%, from about 10% to about 25%, from about 10% to about 30%, from about 10% to about 35%, from about 10% to about 40%, from about 10% to about 45%, from 10% to about 50%, from about 15% to about 20%, from about 15% to about 25%, from about 15% to about 30%, from about 15% to about 35%, from about 15% to about 40%, from about 15% to about 45%, from 15% to about 50%, from about 20% to about 25%, from about 20% to about 30%, from about 20% to about 35%, from about 20% to about 40%, from about 20% to about 45%, from 20% to about 50%, from about 25% to about 30%, from about 25% to about 35%, from about 25% to about 40%, from about 25% to about 45%, from 25% to about 50%, from about 30% to about 35%, from about 30% to about 40%, from about 30% to about 45%, from 30% to about 50%, from about 35% to about 40%, from about 35% to about 45%, from about 35% to about 45%, from 35% to about 50%, from about 40% to about 45%, from 40% to about 50%, or from 45% to about 50% over an immersion period of from 5 days to 10 days, from 5 days to 15 days, from 5 days to 20 days, from 5 days to 25 days, from 5 days to 30 days, from 5 days to 35 days, from 5 days to 40 days, from 10 days to 15 days, from 10 days to 20 days, from 10 days to 25 days, from 10 days to 30 days, from 10 days to 35 days, from 10 days to 40 days, from 15 days to 20 days, from 15 days to 25 days, from 15 days to 30 days, from 15 days to 35 days, from 15 days to 40 days, from 20 days to 25 days, from 20 days to 30 days, from 20 days to 35 days, from 20 days to 40 days, from 25 days to 30 days, from 25 days to 35 days, from 25 days to 40 days, from 30 days to 35 days, from 30 days to 40 days, or from 35 days to 40 days.

The materials and implants according to embodiments of the present invention may be configured for use as any medical implants known in the art constructed from magnesium or its alloys. In some embodiments, implants of the present invention are useful as bone implants, fixation devices, and/or for osteosynthesis. In some embodiments, the implants of the present invention are configured to be biodegradable. In some embodiments, the present invention includes a bone plate made from the materials disclosed herein. In some embodiments, the bone plate of the present invention is constructed from magnesium or its alloys. In some embodiments, the bone plate is entirely or at least partially coated with a coating or ceramic layer as described herein. In some embodiments, the bone plate is only partially coated. Bone plates according to some embodiments of the present invention are configured for attachment to one or more bones or bone fragments and may have any general shape known in the art suitable for bone fixation, osteosynthesis, compression and/or bone fusion. In some embodiments, the bone plates include one or more fixation holes for receiving a bone screw, tack, nail, or other fixation device for attachment to bone. In some embodiments, the bone plates may have a substantially linear or longitudinal configuration. In some embodiments, for example, the bone plate may have a plurality of fixation holes that are arranged substantially linearly or in a single row. In other embodiments, the bone plate may include a plurality of fixation holes that are arranged in a plurality of rows, for example, in a two dimensional array.

FIGS. 16A-16D illustrate example bone plates 100, 110, 120, and 130 according to embodiments of the invention, showing different possible configurations. Bone plates 100, 110, 120, and 130 may include one or more holes for receiving fixation devices, for example, bone screws 102, 112, 122, and 132. In some embodiments, bone plates 100, 110, 120, and 130 are made from magnesium or a biocompatible magnesium alloy and may be entirely or at least partially coated with a ceramic coating or layer as described herein. In some embodiments, bone plates 100, 110, 120, and 130 are only partially coated. In some embodiments, bone screws 102, 112, 122, and 132 are made from the same materials as bone plates 100, 110, 120, and 130, respectively. In some embodiments, bone screws 102, 112, 122, and 132 are made from magnesium or a biocompatible magnesium alloy and may be entirely or at least partially coated with a ceramic coating or layer as described herein. In some embodiments, the portions of bone plates 100, 110, 120, and 130 and/or bone screws 102, 112, 122, and 132 to be coated are coated by exposure to an aqueous electrolyte bath containing, consisting of, or consisting essentially of ammoniac, diammonium hydrogen phosphate, and urea as described herein.

Figure 17A:
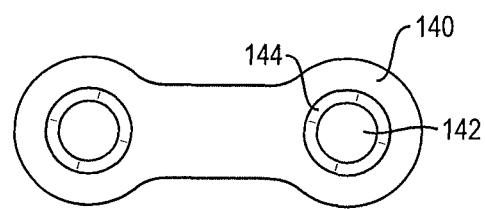
FIGS. 17A and 17B show other example bone plate configurations in accordance with further embodiments of the invention.
Figure 17B:
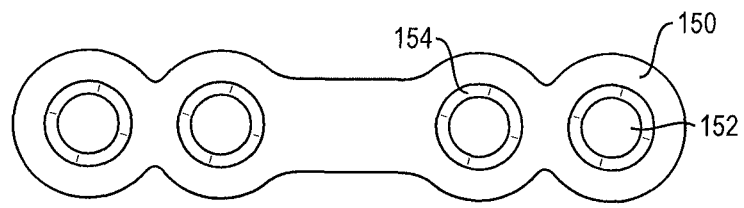

FIGS. 17A and 17B illustrate further example bone plates 140 and 150 according to embodiments of the invention. In some embodiments, bone plates 140 and 150 respectively include holes 142 and 152 for receiving fixation devices (not shown), such as a bone screw, nail, or tack. In some embodiments, bone plates 140 and 150 may further include countersinking 144 and 154 around holes 142 and 152. In some embodiments, bone plates 140 and 150 may be constructed from magnesium or a biocompatible magnesium alloy. In some embodiments, bone plates 140 and 150 are entirely or at least partially coated with a ceramic coating or layer as described herein. In some embodiments, bone plates 140 and 150 are only partially coated. For example, in some embodiments, the internal surfaces of holes 142 and 152 remain uncoated. In some embodiments, countersinking 144 and 154 remain uncoated. In some embodiments, the portions of bone plates 140 and 150 to be coated are coated by exposure to an aqueous electrolyte bath containing, consisting of, or consisting essentially of ammoniac, diammonium hydrogen phosphate, and urea as described herein.

Other example bone plate configurations that may be used according to some embodiments of the present invention may be found in U.S. Patent Application Publication Nos. US 2003/0004515 A1 and US 2008/0009872 A1, which are each incorporated herein by reference in its entirety.

These and other aspects of the present invention will be further appreciated upon consideration of the following Examples, which are intended to illustrate certain particular embodiments of the invention but are not intended to limit its scope, as defined by the claims.

EXAMPLE 1

Lean Electrolyte Compositions

Coatings were made on rectangular magnesium plates with 10 cm$^2$ surface area immersed in selected electrolyte compositions, using a direct current of 0.16 A, a maximum tension of 400 V and a coating time of 10 minutes. The electrolyte compositions used are as follows:

Composition of electrolyte A: 0.13 mol/L diammonium hydrogen phosphate, 1.07 mol/L ammoniac (25%), and 0.50 mol/L urea.

Composition of electrolyte B: 0.05 mol/L diammonium hydrogen phosphate, 5.36 mol/L ammoniac (25%), and 0.50 mol/L urea.

Figure 2:
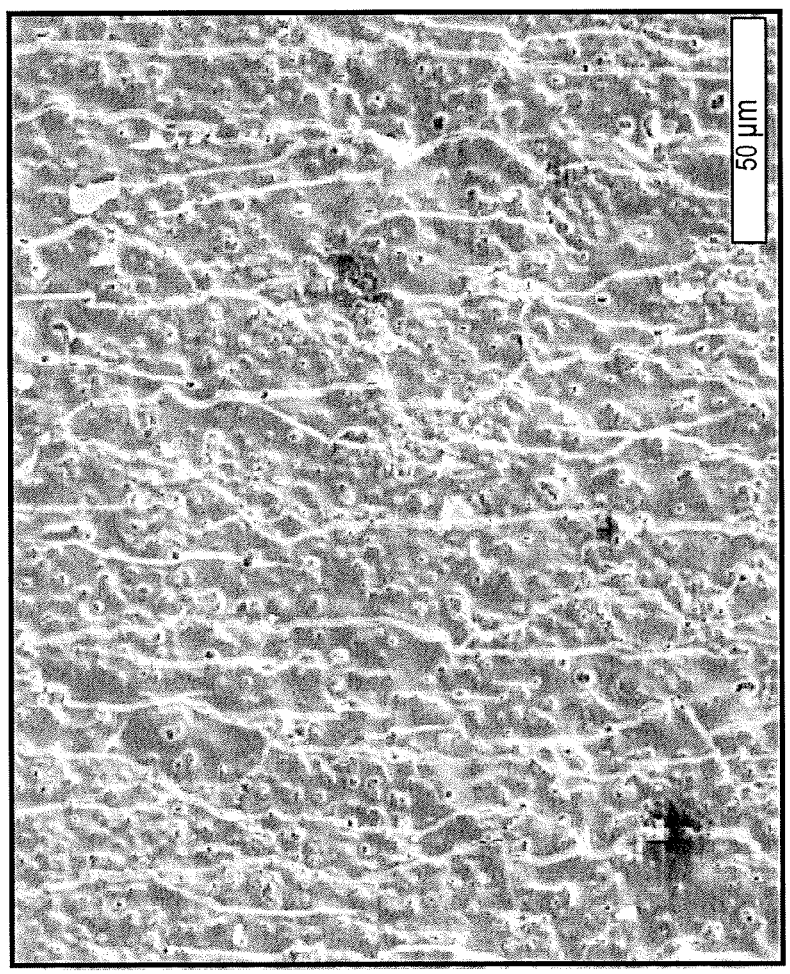
FIG. 2 is an SEM image of a coating according to another embodiment of the invention with fine pores.

FIG. 1 shows an SEM image of a coating on a magnesium plate with coarse pores produced using electrolyte A, after plastic deformation. FIG. 2 shows an SEM image of a coating on a magnesium plate with fine pores produced using electrolyte B, after plastic deformation. The composition of the electrolyte was the major parameter for the pore size as all other parameters were identical between the two samples.

The size and distribution of the pores may be important for the failure behavior of the implant. After plastic deformation and elastic tensioning, the sample with the coarse pores (FIG. 1) shows broader cracks than the sample with fine pores (FIG. 2) where the cracks are finer and more evenly distributed. It is presumed that corrosion attack may be more localized with the coarser pores, which might also act as stress risers.

EXAMPLE 2

In Vivo Degradation

Experiment:
All animal experiments were conducted in accordance with the Swiss animal protection law. Fourteen skeletally mature miniature pigs each with an age of 30 to 36 months and an average weight of 53±7 kg were used in this preliminary study.

Figure 3:
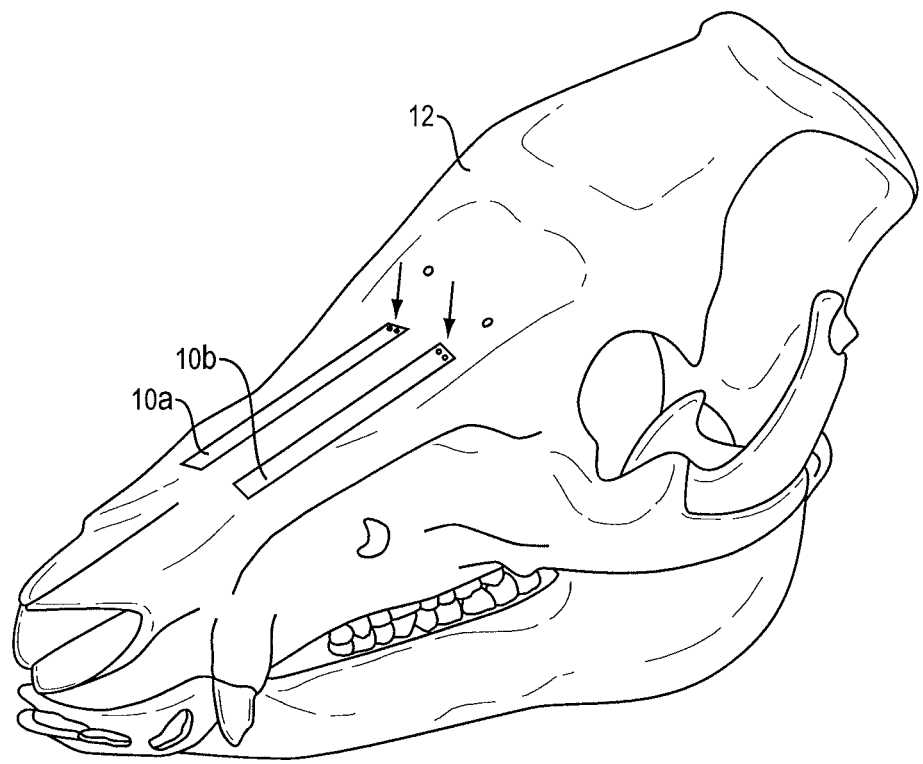
FIG. 3 illustrates the position of implanted strength retention plates according to an embodiment of the invention on a miniature pig nasal bone.

The midface of the miniature pig is approached by a T-type incision where as a median cut of 11-12 cm length was started about 2 cm below the lower orbits. After exposing the frontal bone, a soft tissue pocket was created with a rasp, big enough to accommodate the two rectangular plates and deep enough to profit of the straight portion of the nasal bone. Pre-bending of the plates could therefore be avoided. FIG. 3 illustrates the positioning of implanted plates 10a and 10b on a pig skull 12 in accordance with this Example. Each miniature pig received either two coated or two non-coated magnesium plates. The coated plates were coated in accordance with Example 3 below.

Figure 7:
FIG. 7 shows an X-ray image of a non-coated magnesium plate according to an embodiment of the invention implanted in a miniature pig after 1 week.
Figure 8:
FIG. 8 shows an X-ray image of a coated magnesium plate according to an embodiment of the invention implanted in a miniature pig before euthanasia at 12 weeks.

In addition to the post-operative X-rays of the head, intermediate radiographs (Philips BVPulsera) were taken at 1, 4, 8, and 12 weeks. FIG. 7 shows an X-ray image of a non-coated magnesium plate implanted in a miniature pig after 1 week. FIG. 8 shows an X-ray image of a coated magnesium plate implanted in a miniature pig at 12 weeks before euthanasia. The animals were sacrificed after 12 and 24 weeks.

After euthanasia, a computed X-ray tomography (CT) was made. A medial incision of about 10 cm length was made along the longitudinal axis of the nose and the implants were removed. The pH of the implant bed was determined using pH sensitive strip (Merck 1.09557.0003, pH range 6.4-8.0) which was moistened with distilled water before use. The removed plates were stored in 70% ethanol in a tightly sealed glass bottle. After transportation to the mechanical testing site, the magnesium plates were removed from the glass bottles, dabbed with paper towel and dried in air.

Energy dispersive X-ray spectroscopy (EDX) measurements were carried out in a Zeiss EVO60 scanning electron microscope (SEM) using a THERMO Scientific ultra dry EDX detector. The measured spectra were analyzed for the elements C, O, Mg, P, Ca, Y, Zr, Nd, Gd, Dy, Er, Yb, Na and K. Chlorine (Cl) was excluded from the analysis as it could not be detected on any of the spectra. Three areas of about 100 µm×100 µm were measured on each sample to determine the EDX-spectra. The weight loss was determined after brushing off the degradation products with a nail brush. Additionally, the plates were immersed in 40% hydrofluoric acid for at least 5 minutes as described by A. Krause et al. ("Degradation behavior and mechanical properties of magnesium implants in rabbit tibiae" *Journal of Materials Science* 2010, 45, 624-632, incorporated herein by reference in its entirety), cleaned in distilled water and ethanol and dried with an air blower.

Results:

The occurrence of gas bubbles might be taken as an indicator for the in vivo degradation. As the exposed surface of the magnesium plates is very large (2×9 cm$^2$), a daily release of about 5 ml might be expected when using the in vitro gas release rate of 0.3 ml/cm$^2$ per day. If this amount of gas could not be transported away, gas bubbles would form in the thick soft tissue on top of the plates. Intermediate X-rays were used to check the occurrence of gas bubbles and the integrity of the rectangular plates. For the non-coated plates, gas bubbles could be observed in most of the animals after 1 week. The large observed gas bubble in the case of one animal disappeared by week 4. For the coated plates, the occurrence of gas bubbles was delayed. First signs of gas pockets often occurred around the thread holes and started to appear by week 4. No signs of loose tissue could be seen around the titanium control plates. The additional CT images show the situation after euthanasia and before the removal of the plates. The plates did not seem to be much corroded upon removal. The plates removed at 24 weeks showed larger areas with white corrosion products than the plates at 12 weeks. The two sides of the plates were not equally corroded; the top side in contact with the soft tissue seemed more corroded than the bottom side in contact with the frontal bone. The plates seemed well integrated to the surrounding tissue as a lateral step seemed to have formed in the bone. On one animal of each 24 week group, the pH of the implant beds was determined after removal of the plate. No difference in pH could be found for the coated and non-coated groups compared to the titanium reference. pH values of 7.0-7.2 were typically found. The white, enamel-like degradation products seemed more compact and more adherent compared to the in vitro situation. As a consequence, the brushing off of the degradation products was not sufficient and additional bathing in hydrofluoric acid was used to determine the total weight loss. For both kind of plates, the average weight loss was about 5-6% after 12 weeks and increased to 13-14% after 24 weeks. The results of the EDX analysis of the in vivo degradation products prior to the brush off showed significantly higher calcium and phosphor contents for the coated magnesium plates for each milligram of corroded metal and are summarized in Table I below.

TABLE I

EDX analysis of degraded implant surface before brushing off degradation products.

| Chemical elements [wt %] | Non-coated 12 weeks | Non-coated 24 weeks | Coated 12 weeks | Coated 24 weeks |
|---|---|---|---|---|
| Carbon | 11 ± 6 | 16 ± 14 | 26 ± 11 | 18 ± 8 |
| Oxygen | 42 ± 5 | 42 ± 9 | 31 ± 5 | 33 ± 3 |
| Magnesium | 13 ± 2 | 13 ± 5 | 3.3 ± 1.3 | 4.2 ± 1.4 |
| Calcium | 2.5 ± 0.7 | 2.6 ± 2.2 | 14 ± 6 | 12 ± 7 |
| Phosphor | 3.8 ± 1.4 | 4.4 ± 4.1 | 12 ± 3 | 10 ± 4 |
| Yttrium, Zirconium & rare earths | 28 ± 2 | 22 ± 2 | 13 ± 7 | 23 ± 16 |

EXAMPLE 3

Alloy and Coating

Based on the composition of the magnesium alloy WE43 (chemical composition: Mg—Y—Nd heavy rare earths), a new alloy was developed. Implants from the same lot were used for all experiments (lot MI0018B, T5 heat treated, 6.4× 19 mm extrusion profile). The rectangular plates with 60 mm×6.0 mm×1.50 mm were machined dry (w/o lubricant) using hard metal tools. All edges were rounded with a radius of 0.5 mm. A total of 36 plates were tested, half of the plates without a coating and the other half with a plasmaelectrolytic coating from AHC (Kerpen, Germany). A standard MAGOXID™ electrolyte was used and a direct current of 1.4 A/dm$^2$ for up to 400 V was applied to generate the coating. Non-coated plates initially weighted 940±5 mg. The MAGOXID™ coating had a typical thickness of 10 µm and accounted for 15 mg of additional mass. The total surface of a plate was 9 cm$^2$. The plates were cleaned with ultrasound assistance in 90-100% ethanol, dried in air, packaged in pairs of two in a double vacuum pouch and γ-sterilized with a dose of 25-30 kGy.

EXAMPLE 4

In Vitro Immersion Testing

Experiment:

Coated and non-coated samples were each tested inside a separate immersion unit containing 250 ml of simulated body fluid (SBF). Coated samples were prepared in accordance with Example 3 above. An immersion unit consisted of a graduated glass cylinder with 25 mm inner diameter and 240 mm length and a 250 ml plastic bottle. Each magnesium sample was put inside the glass cylinder which was then filled with SBF. The plastic bottle was put upside down over the glass cylinder. The cylinder/bottle assembly was quickly tilted to avoid the flowing out of the liquid and the remaining SBF was poured into the gap between bottle and glass cylinder. Finally, the lid of the bottle—which had a 33 mm hole—was slid over the glass cylinder to fix the assembly. The bottles were put inside a tempered water bath at 37° C.

The simulated body fluid was prepared from stock solutions as described by L. Müller and F. A. Müller ["Preparation of SBF with different $HCO_3^-$ content and its influence on the composition of biomimetic apatites" *Acta Biomaterialia* 2 (2006) 181-9, incorporated herein by reference in its entirety] with TRIS buffer and the recipe for a $HCO_3$— content of 27 mmol/L. The addition of $NaN_3$ was omitted as no bacterial growth was observed and as $N_2$ release into the medium could be avoided. The medium was changed once a week. Identical material lots, coatings and geometries were used for the in vitro and the in vivo degradation tests. The samples were immersed for 4, 8 and 12 weeks. The gas release was determined by regular visual inspection of the graded glass cylinders with a precision of about ±1 ml. The average mass loss was determined at the end of the immersion period by brushing off the corrosion products with a common nail brush.

Figure 5:
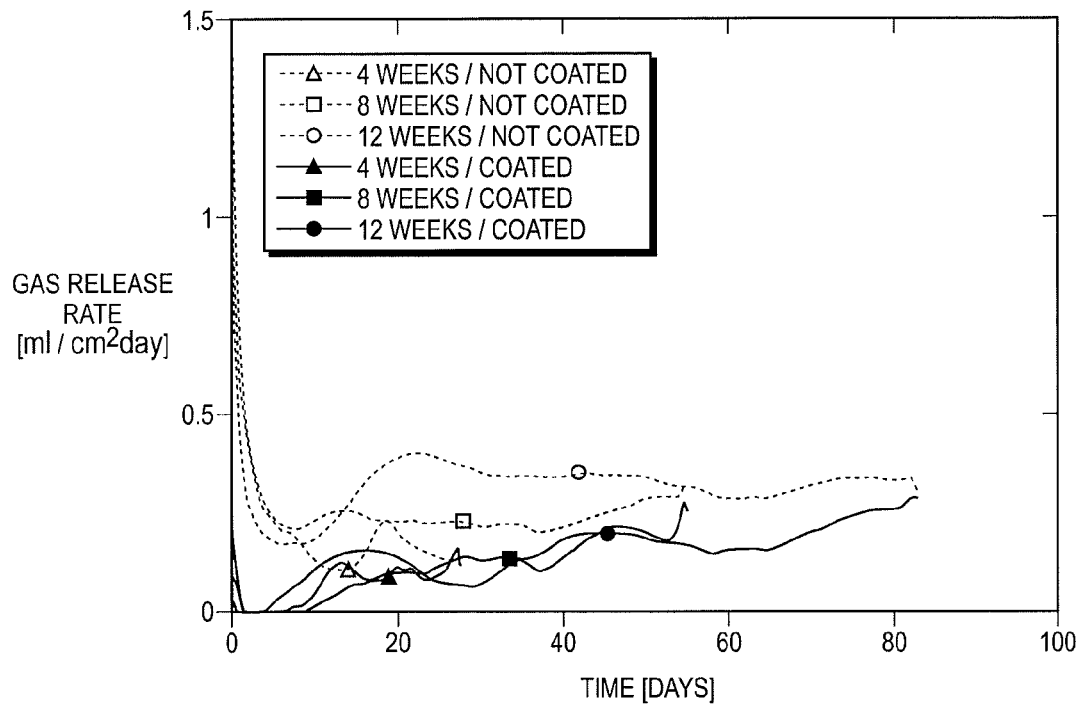
FIG. 5 shows average gas release rate of coated and non-coated rectangular plates according to certain embodiments of the invention immersed in simulated body fluid (SBF) for up to 12 weeks (average of 6 tests per data point)
Figure 6:
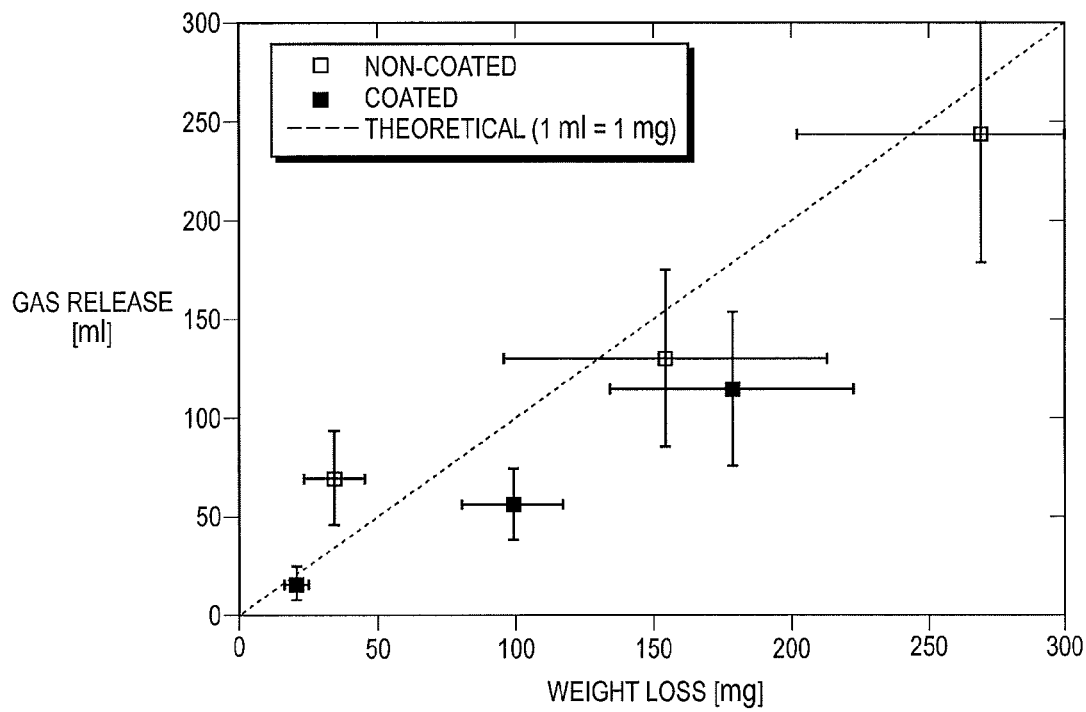
FIG. 6 shows gas release as a function of weight loss of coated and non-coated rectangular plates according to certain embodiments of the invention immersed in SBF for up to 12 weeks (average of 6 tests per data point)

Results:

The average gas release during immersion in SBF can be seen in FIG. 5, which shows a graph depicting the average gas release rate of coated and non-coated rectangular plates immersed in SBF for up to 12 weeks (average of 6 tests per data point). The non-coated samples started to release gas directly after immersion. Initial gas release rates were highest during the first couple of days (>1 ml/cm² per day) and then stabilized around 0.3 ml/cm² per day. On the other hand, the coated samples showed nearly no gas release during the first two weeks. The gas release rates then started to increase and stabilized around 0.2 ml/cm² per day. The degradation of non-coated magnesium samples was uniform over the entire immersion time. Some localized corrosion seemed to occur for the coated magnesium samples at 12 weeks which might be associated with a slight increase in the gas release rate around day 65 (9-10 weeks). The mass loss of the samples— determined by brushing off the powder-like white corrosion products—could be put into relation with the observed gas release as shown in FIG. 6, which is a graph depicting gas release as a function of weight loss of coated and non-coated plates immersed in SBF for up to 12 weeks (average of 6 tests per data point). For the non-coated samples, about 1 ml of gas is released for 1 mg of corroded magnesium as theoretically expected from the overall corrosion reaction. For the coated magnesium, however, less gas was released than expected; only around 0.6 ml of gas could be collected

EXAMPLE 5

Mechanical Testing

Figure 4:
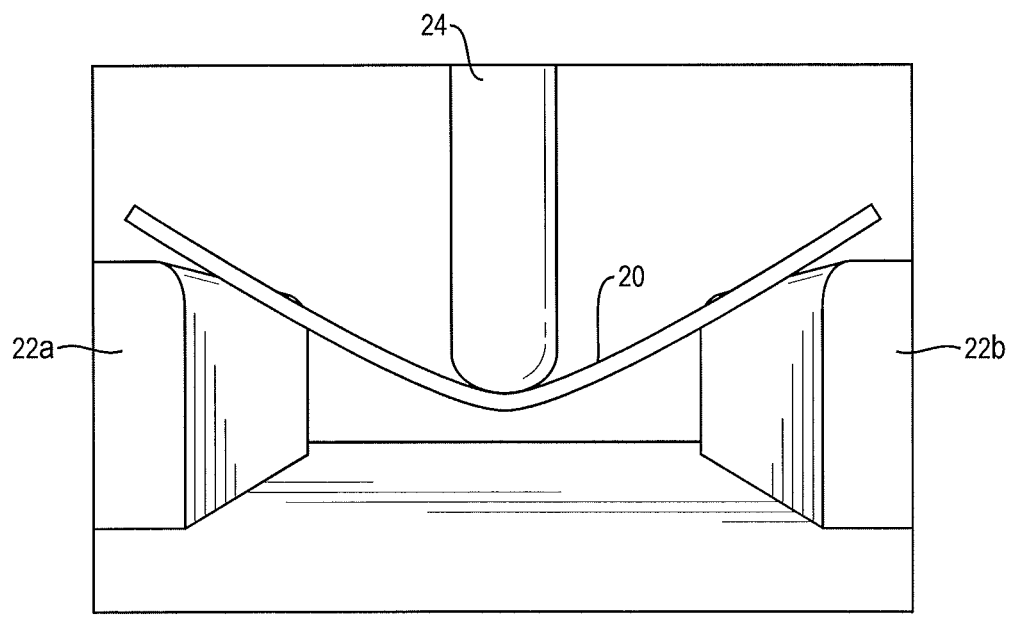
FIG. 4 illustrates a 3-point-bending test of a degraded rectangular plate according to an embodiment of the invention.

Experiment:

The 3-point-bending tests of the in vivo and in vitro degraded samples from Examples 2 and 4 were made using a small Zwick/Roell universal testing machine (type BZ2.5/TN1S) with a test device according to ISO EN 178. FIG. 4 illustrates a depiction of the 3-point-bending test showing a sample 20 positioned on two support brackets 22a and 22b being bent by a downward moving plunger 24. A span of 40 mm was used for all the plates. The support brackets had a radius of 2 mm. The plunger was 4 mm in diameter and was moved downwards at a rate of 1 mm/min. The test was stopped after 10 mm of displacement. Forces were recorded with a precision of ±0.5% (2 kN force gauge).

Figure 9:
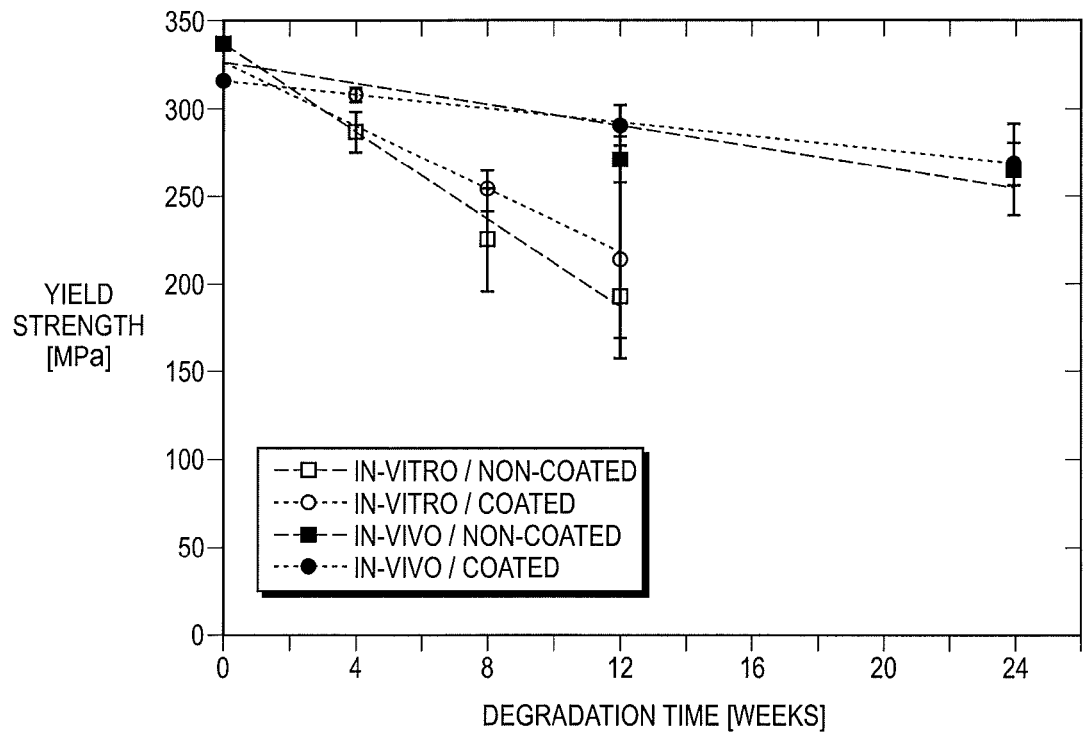
FIG. 9 shows decrease of yield strength for in vitro and in vivo degraded rectangular plates according to certain embodiments of the invention.

Results:

The measured maximum bending force, bending stress, yield strength and flexural modulus are given in Table II for the non-coated and in Table III for the coated implants below. Each value averages 6 samples, from individual bottles for the in vitro case and from 3 different animals in the in vivo case (pairs of two). FIG. 9 is a graph further showing the decrease of yield strength over time for in vitro and in vivo degraded coated and non-coated rectangular plates.

TABLE II

Strength retention of non-coated rectangular magnesium plates after in vitro and in vivo degradation.

| Mechanical property Time point | Maximum bending force [N] | Maximum flexural strength [MPa] | Flexural modulus [GPa] | Yield strength [MPa] |
|---|---|---|---|---|
| Titanium | 213 | 972 | 100 | 805 |
| Non degraded | 91.6 ± 1.2 | 402 ± 5 | 41.5 ± 0.5 | 336 ± 2 |
| In vitro 4 weeks | 82.9 ± 3.1 | 361 ± 16 | 32.0 ± 2.0 | 285 ± 12 |
| In vitro 8 weeks | 61.3 ± 9.0 | 279 ± 38 | 24.4 ± 3.7 | 224 ± 30 |
| In vitro 12 weeks | 48.9 ± 8.7 | 241 ± 30 | 18.7 ± 3.8 | 192 ± 24 |
| In vivo 12 weeks | 86.7 ± 4.6 | 367 ± 20 | 29.5 ± 2.4 | 270 ± 13 |
| In vivo 24 weeks | 80.0 ± 6.4 | 346 ± 33 | 28.0 ± 4.8 | 264 ± 26 |

TABLE III

Strength retention of coated rectangular magnesium plates after in vitro and in vivo degradation.

| Mechanical property Time point | Maximum bending force [N] | Maximum flexural strength [MPa] | Flexural modulus [GPa] | Yield strength [MPa] |
|---|---|---|---|---|
| Non degraded | 91.5 ± 2.0 | 393 ± 7 | 39.2 ± 0.6 | 316 ± 4 |
| In vitro 4 weeks | 102.4 ± 5.6 | 437 ± 24 | 35.5 ± 0.8 | 308 ± 3 |
| In vitro 8 weeks | 73.6 ± 3.5 | 332 ± 15 | 28.6 ± 1.9 | 252 ± 12 |
| In vitro 12 weeks | 60.2 ± 20.8 | 280 ± 92 | 24.7 ± 3.6 | 213 ± 57 |
| In vivo 12 weeks | 92.7 ± 3.9 | 394 ± 16 | 33.3 ± 1.8 | 290 ± 12 |
| In vivo 24 weeks | 83.9 ± 3.9 | 363 ± 21 | 27.9 ± 3.9 | 268 ± 12 |

All in vivo degraded plates could be deformed to the final bending position without breaking. In addition to those 3-point-bending tests on in vivo and in vitro degraded plates, the chosen 3-point-bending setup with a constant span of 40 mm was verified with a series of rectangular plates to check if the changed dimensions of the degraded plates would give correct strength measurements. A uniform degradation was "simulated" by decreasing the thickness and width of the plates in 0.2 mm steps down to a thickness of 0.5 mm and to a width of 5.0 mm. According to theory, the bending force F is expected to depend on the thickness d and on the width b as follows:

$$F = \frac{2}{3}\frac{\sigma_b}{L}bd^2$$

with the span L and the bending stress $\sigma_b$. When assuming a constant bending stress, $\sigma_b$=MPa, an excellent fit between the measured maximum forces (results not shown) and the theoretical values was obtained ($\Delta F \leq 2$ N). This relation might be used to calculate the core thickness of a degraded plate and to assess the uniformity of degradation.

EXAMPLE 6

Anodic Oxidation

Experiment:

The magnesium implant of WE43 alloy used in this experiment had a surface of 0.1 dm$^2$. It was degreased, pickled and rinsed with aseptic water. The WE43 alloy was treated with an aqueous electrolyte bath consisting of:

1.07 mol/L ammoniac (25%) (80 ml/L);
0.13 mol/L diammonium hydrogen phosphate; and
0.5 mol/L urea.

The magnesium implant was hung into the aqueous electrolyte bath and the positive pole was connected to a D.C. current source. A sheet of stainless steel was also put inside the aqueous electrolyte bath and was connected to the negative pole of the D.C. current source. The current density was set to 1.4 A/dm$^2$. The "ceramization" of the magnesium implant was carried out for 8 minutes. The final voltage was set to 360 V.

Results:

The obtained ceramic layer had a thickness of 11 µm. The "ceramized" magnesium implant was taken out of the electrolyte bath and was rinsed well with aseptic, de-ionised water and subsequently dried. Chemical analysis of the produced ceramic layer on the WE43-magnesium implant showed MgO, Mg(OH)$_2$ and small amounts of Mg$_3$(PO$_4$)$_2$, Yttrium oxide and oxides of rare earth elements.

Other magnesium wrought alloys such as WE54, ZK40, ZK, 60, AZ31 as well as magnesium cast alloys such as AZ91, AM50, AS41 can similarly be ceramized (with stainless steel and platinum as cathode materials, for example) with the procedure of Example 6.

EXAMPLE 7

In Vitro Degradation Behavior of WE43 Samples

Figure 10:
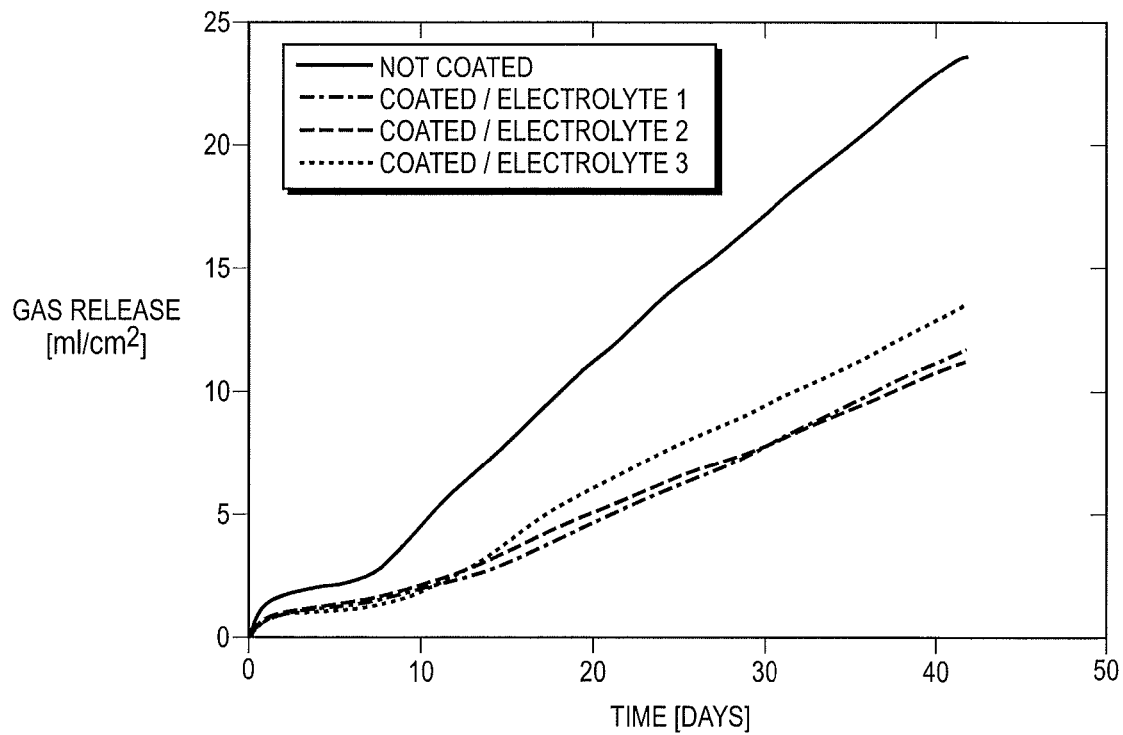
FIG. 10 shows in vitro degradation behavior of non-coated WE43 magnesium alloy samples and WE43 magnesium alloy samples coated according to certain embodiments of the invention, during immersion in simulated body fluid (SBF)

Experiment:

In vitro degradation behavior of non-coated and coated WE43 magnesium alloy samples during immersion in simulated body fluid (SBF) is shown FIG. 10. Magnesium WE43 samples with coatings from three different electrolytes exhibit a significantly reduced hydrogen release compared to non-coated WE43 alloy samples. The three electrolytes contained the following:

Electrolyte 1: diammonium hydrogen phosphate and ammoniac.
Electrolyte 2: diammonium hydrogen phosphate, ammoniac, and urea.
Electrolyte 3: citric acid, boric acid, phosphoric acid, and ammoniac.

EXAMPLE 8

Gas Release and Strength Retention of Tensioned WE43 Samples Immersed in SBF Experiment:

Rectangular samples of WE43 alloy (60 mm×8.0 mm×0.50 mm) were dry machined (w/o lubricant) using hard metal tools. A portion of the samples were coated with a plasmaelectrolytic coating from AHC (Kerpen, Germany). The electrolyte compositions used for the plasmaelectrolytic coating are variations of the standard MAGOXID™ electrolyte. A direct current of 1.4 A/dm$^2$ for up to 400 V was applied to generate the coating. Other sample lots were coated using different lean electrolytes comprising varying percentages of diammonium hydrogen phosphate, ammoniac (at 25 vol. % concentration), and urea, the ratios of which are shown in Table IV below.

Figures 14A, 14B:
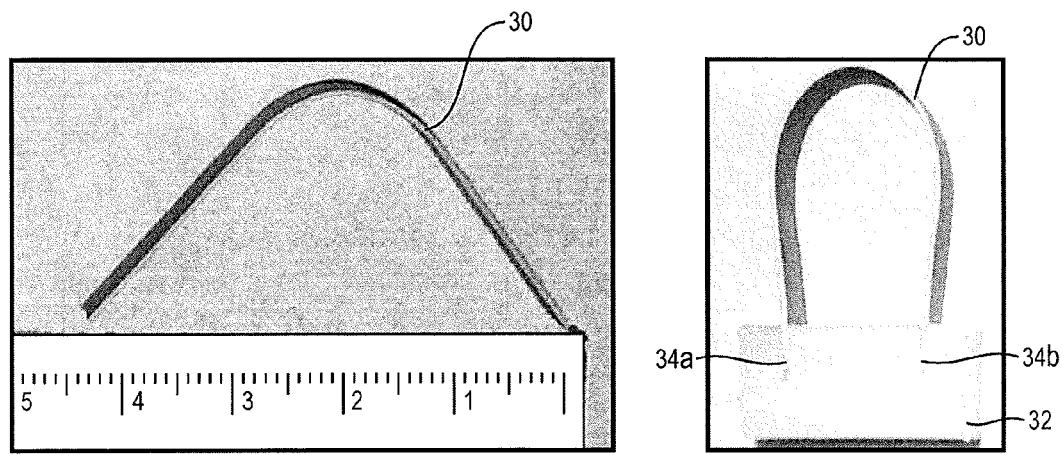
FIG. 14A shows an example WE43 magnesium alloy sample, treated in accordance with an embodiment of the invention, after plastic deformation around a 16 mm diameter cylinder.
FIG. 14B shows an example WE43 magnesium alloy sample, treated in accordance with an embodiment of the invention, after tensioning and positioning in a sample holder.
Figure 15D:
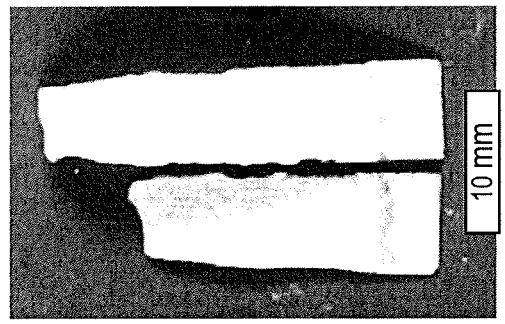
FIG. 15D shows the WE43 magnesium alloy sample of FIG. 15C after removal from the holder.
Figure 15C:
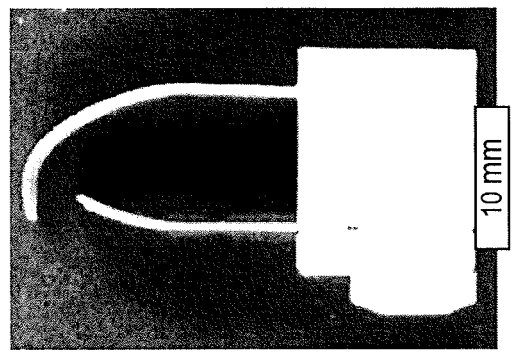
FIG. 15C shows the WE43 magnesium alloy sample of FIG. 15B after six weeks of immersion in SBF.
Figure 15B:
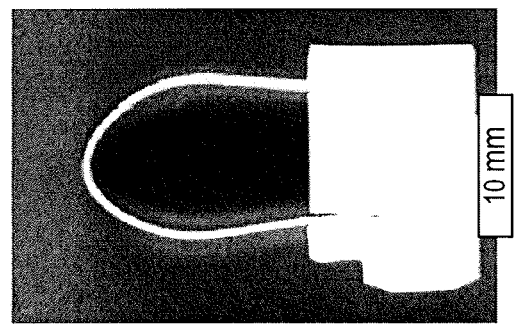
FIG. 15B shows an example WE43 magnesium alloy sample, treated in accordance with an embodiment of the invention, in a holder with screw fixation for strength retention testing prior to immersion in SBF.
Figure 15A:
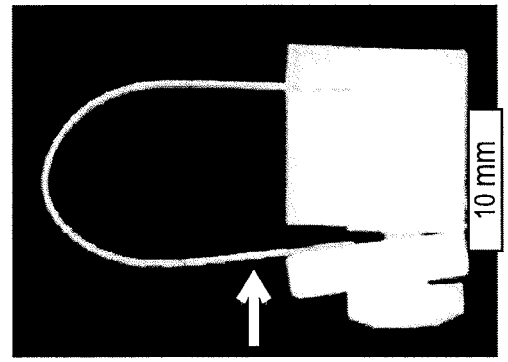
FIG. 15A shows an example WE43 magnesium alloy sample, treated in accordance with an embodiment of the invention, positioned in a holder with screw fixation for strength retention testing.
Figure 16A:
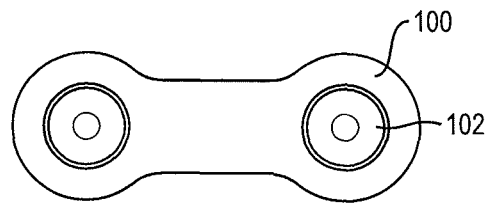
FIGS. 16A-16D show example bone plate configurations in accordance with some embodiments of the invention.
Figure 16B:
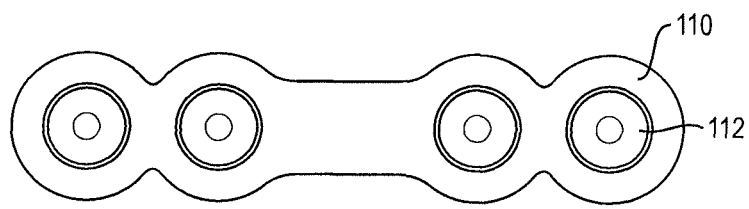
Figure 16C:
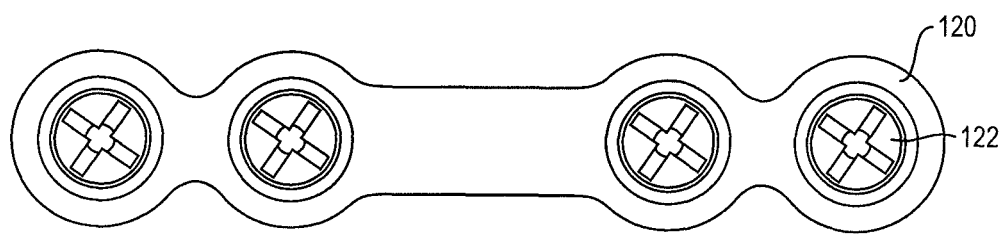
Figure 16D:
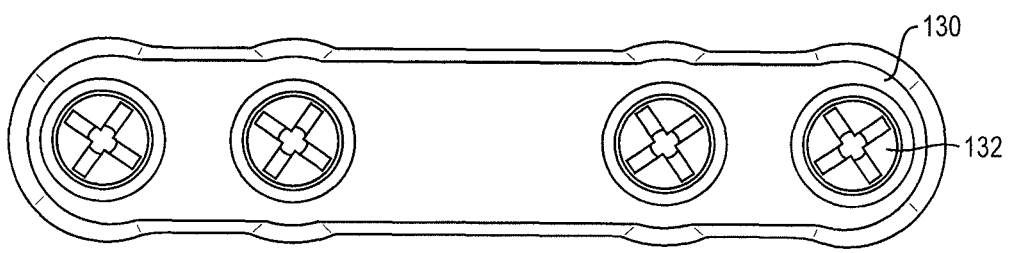

The rectangular samples were manually deformed by bending the ends around a cylinder with a 16 mm diameter. The amount of bending is defined by the span of the two ends of the rectangular sample in a relaxed state. A span of about 42 mm was applied to the samples as shown in FIG. 14A, which depicts an example of a manually deformed sample 30. The bent samples were then put under tension by inserting each of the ends of a sample into slots spaced about 12 mm apart in a UHMWPE sample holder. FIG. 14B shows example sample 30 after the ends of which have been inserted into slots 34a and 34b of sample holder 32 under tension.

Immersion tests of the tensioned were performed by placing tensioned samples inside separate immersion units containing 250 ml of SBF in a manner similar to the process described in Example 4 for a total of six weeks. The 250 ml of SBF was exchanged once a week. Gas levels were recorded twice on working days and occurrence of failure was visually checked for the samples.

Strength retention tests were also carried out on immersed samples using sample holders with screw fixation (FIG. 15A-15D). During the weekly SBF changes, the screw of the holder is loosened and the spring force above the holder is measured by a push pin (indicated by the arrow in FIG. 15A). The samples did not need to be removed from the holder during the procedure. The samples were left in the SBF for 6 weeks irrespective of eventual failure (breakage) of the sample (e.g., shown in FIGS. 15C and 15D).

Figure 11:
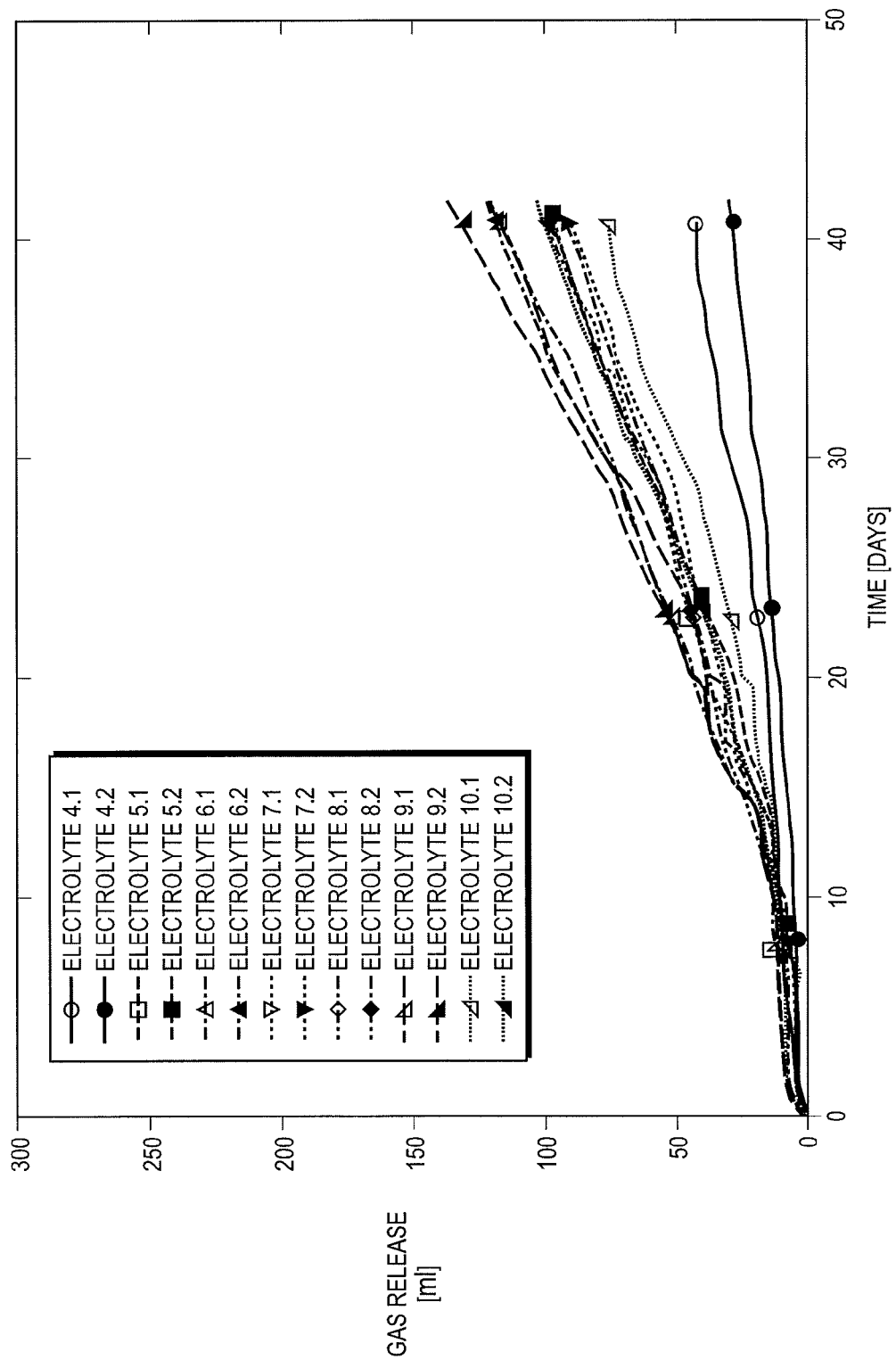
FIG. 11 shows average accumulated gas release of tensioned WE43 magnesium alloy samples, treated in accordance with certain embodiments of the invention, during immersion in SBF.
Figure 12:
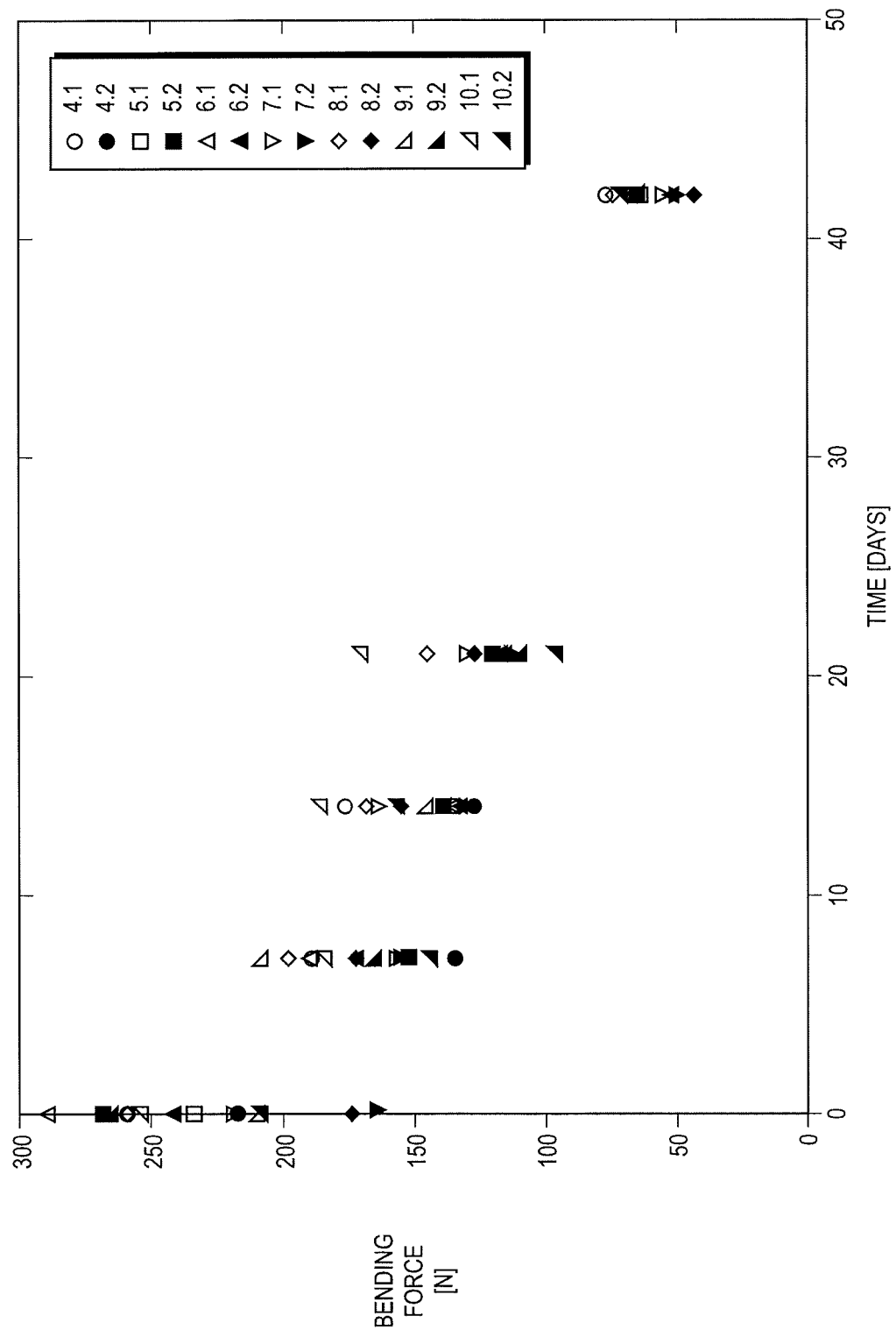
FIG. 12 shows strength retention (remaining bending force) measurements of tensioned WE43 magnesium alloy samples, treated in accordance with certain embodiments of the invention, during immersion in SBF.

Results:

All the tested coatings had an excellent adherence to the base material and did not delaminate during the large plastic deformation applied to the samples. Plastic deformation did introduce microcracks into the coating which broadened during the additional tensioning and allowed greater access to the corrosive SBF medium. Despite the severe testing conditions, the gas release rates of the lean electrolyte-coated samples were found to be between about 0.2 ml/cm$^2$ per day and about 0.4 ml/cm$^2$ per day, and were generally below the values for the non-coated base material which ranged from about 0.4 ml/cm$^2$ per day to about 0.6 ml/cm$^2$ per day. The average accumulated gas release of the lean electrolyte-coated rectangular samples under tension and immersed in SBF over time is shown in the graph of FIG. 11. The strength retention measurements of the lean electrolyte-coated samples is shown in FIG. 12, which is a graph depicting remaining bending force as a function of immersion time.

Figure 13:
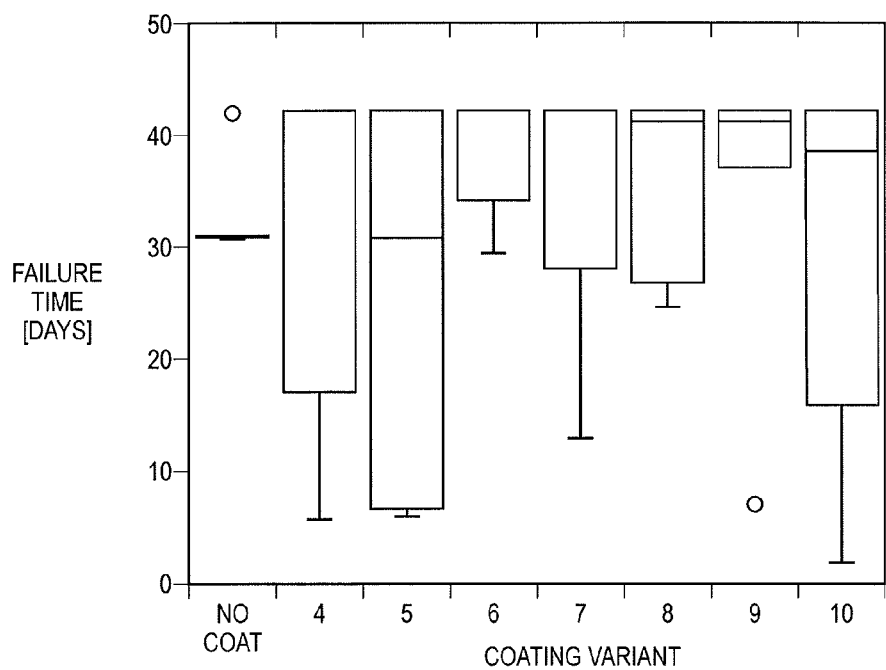
FIG. 13 shows failure times as a function of coating variants (6 specimens per variant) according to certain embodiments of the invention on WE43 magnesium alloy samples.

The failure times of tensioned rectangles during immersion in SBF are shown in the box plot of FIG. 13, which illustrates differences between the various coatings. Four of the five non-coated samples failed after 32 days of immersion. The specimens coated with the lean electrolytes showed a larger degree of variance with some samples withstanding the 42 days of immersion without failing while others failed prior to the non-coated samples. The strength retention (remaining bending force) testing, which was applied only to the coated samples, may have accelerated the failure of the coated samples compared to the non-coated samples. Moreover, variations in the manual force applied to bend and tension the samples may have contributed to the wider scatter of results. Additional time to failure and gas release rate data for the lean electrolyte-coated samples are provided in Table IV below.

TABLE IV

| electrolyte block | diammonium hydrogen phosphate [%] | ammoniac [%] | urea [%] | time to failure [days] | gas release linear regression | hydrogen release rate [mg/cm²day] | average time to failure [days] |
|---|---|---|---|---|---|---|---|
| 4.1 | 48.15 | 14.81 | 37.04 | 16.9 | 1.67 | 0.22 | 21.6 |
| | 48.15 | 14.81 | 37.04 | 5.8 | 2.65 | | |
| | 48.15 | 14.81 | 37.04 | 42.0 | 2.13 | | |
| 5.1 | 38.61 | 35.91 | 25.48 | 6.7 | 2.29 | 0.23 | 10.7 |
| | 38.61 | 35.91 | 25.48 | 19.7 | 2.20 | | |
| | 38.61 | 35.91 | 25.48 | 5.8 | 2.26 | | |
| 6.1 | 20.00 | 80.00 | 0.00 | 29.2 | 3.36 | 0.29 | 37.1 |
| | 20.00 | 80.00 | 0.00 | 42.00 | 2.43 | | |
| | 20.00 | 80.00 | 0.00 | 40.00 | 2.89 | | |
| 7.1 | 83.33 | 16.67 | 0.00 | 42.0 | 2.06 | 0.22 | 32.2 |
| | 83.33 | 16.67 | 0.00 | 12.7 | 2.19 | | |
| | 83.33 | 16.67 | 0.00 | 42.0 | 2.26 | | |
| 8.1 | 17.24 | 13.79 | 68.97 | 42.0 | 1.06 | 0.23 | 41.3 |
| | 17.24 | 13.79 | 68.97 | 42.0 | 2.54 | | |
| | 17.24 | 13.79 | 68.97 | 40.0 | 3.26 | | |
| 9.1 | 18.52 | 44.44 | 37.04 | 42.0 | 2.50 | 0.29 | 30.3 |
| | 18.52 | 44.44 | 37.04 | 42.0 | 3.48 | | |
| | 18.52 | 44.44 | 37.04 | 7.0 | 2.66 | | |
| 10.1 | 52.00 | 48.00 | 0.00 | 2.0 | 1.19 | 0.18 | 19.9 |
| | 52.00 | 48.00 | 0.00 | 15.8 | 2.52 | | |
| | 52.00 | 48.00 | 0.00 | 42.0 | 1.64 | | |
| 4.2 | 48.15 | 14.81 | 37.04 | 42.0 | 2.44 | 0.26 | 42.0 |
| | 48.15 | 14.81 | 37.04 | 42.0 | 2.87 | | |
| | 48.15 | 14.81 | 37.04 | 42.0 | 2.36 | | |
| 10.2 | 52.00 | 48.00 | 0.00 | 42.0 | 2.41 | 0.28 | 39.6 |
| | 52.00 | 48.00 | 0.00 | 34.7 | 3.00 | | |
| | 52.00 | 48.00 | 0.00 | 42.0 | 2.99 | | |
| 8.2 | 17.24 | 13.79 | 68.97 | 24.7 | 3.35 | 0.32 | 31.1 |
| | 17.24 | 13.79 | 68.97 | 26.7 | 3.74 | | |
| | 17.24 | 13.79 | 68.97 | 42.0 | 2.57 | | |
| 5.2 | 38.61 | 35.91 | 25.48 | 42.0 | 2.80 | 0.28 | 42.0 |
| | 38.61 | 35.91 | 25.48 | 42.0 | 2.71 | | |
| | 38.61 | 35.91 | 25.48 | 42.0 | 2.79 | | |
| 9.2 | 18.52 | 44.44 | 37.04 | 37.0 | 4.15 | 0.36 | 39.7 |
| | 18.52 | 44.44 | 37.04 | 41.0 | 3.18 | | |
| | 18.52 | 44.44 | 37.04 | 41.0 | 3.53 | | |
| 6.1 | 20.00 | 80.00 | 0.00 | 42.0 | 3.46 | 0.33 | 38.9 |
| | 20.00 | 80.00 | 0.00 | 34.1 | 3.48 | | |
| | 20.00 | 80.00 | 0.00 | 40.7 | 2.81 | | |
| 7.2 | 83.33 | 16.67 | 0.00 | 42.0 | 2.55 | 0.26 | 37.3 |
| | 83.33 | 16.67 | 0.00 | 27.8 | 2.93 | | |
| | 83.33 | 16.67 | 0.00 | 42.0 | 2.28 | | |

It should be understood that various changes, substitutions, and alterations can be made herein without departing from the spirit and scope of the invention as defined by the appended claims. It should also be apparent that individual elements identified herein as belonging to a particular embodiment may be included in other embodiments of the invention. Moreover, the scope of the present application is not intended to be limited to the particular embodiments of the process, machine, manufacture, and composition of matter, means, methods and steps described in the specification. As one of ordinary skill in the art will readily appreciate from the disclosure herein, processes, machines, manufacture, composition of matter, means, methods, or steps, presently existing or later to be developed that perform substantially the same function or achieve substantially the same result as the corresponding embodiments described herein may be utilized according to the present invention.

The invention claimed is:

1. A method of producing ceramic layers on magnesium and its alloys, comprising the steps of:
    immersing an implant and a metal sheet into an aqueous electrolyte bath, said aqueous electrolyte bath consisting essentially of: ammoniac, diammonium hydrogen phosphate and urea, and wherein the implant is made of magnesium or its alloy;
    performing an anodic oxidation by passing a current between the implant, the metal sheet and through the aqueous electrolyte bath, wherein the implant is connected to a positive pole of a current source and the metal sheet is connected to a negative pole of the current source;
    applying a current density selected to form sparks on said implant, to thereby form a ceramic layer on said implant.

2. The method according to claim 1, wherein the ammoniac concentration at 25 vol. % ranges from 1.0 mol/L to 6.0 mol/L, the diammonium hydrogen phosphate concentration ranges from 0.05 mol/L to 0.2 mol/L; and the urea concentration ranges from 0.01 mol/L to 1.0 mol/L.

3. The method according to claim 1, wherein the aqueous electrolyte bath has a pH value ranging from 10.3 to 11.6 and a temperature ranging from 18° C. to 22° C.

4. The method according to claim 1, wherein the current density is at least 1 A/dm².

5. The method according to claim 1, wherein the current density ranges from 1 A/dm² to 3 A/dm².

6. The method according to claim 1, further comprising electrically insulating areas of a surface of the implant which are not to be coated such that a coating of the ceramic layer is selectively applied to the implant.

7. The method according to claim 6, wherein electrically insulating the areas which are not to be coated is achieved by applying a lacquer, film, or foil to the areas of the surface of the implant which are not to be coated prior to immersing the implant into said aqueous electrolyte bath.

* * * * *